US009119773B2

United States Patent
Smyth et al.

(10) Patent No.: US 9,119,773 B2
(45) Date of Patent: Sep. 1, 2015

(54) TOROIDAL PHARMACEUTICAL FORMULATIONS

(75) Inventors: Hugh Smyth, Austin, TX (US); Matthew Herpin, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 193 days.

(21) Appl. No.: 13/535,069

(22) Filed: Jun. 27, 2012

(65) Prior Publication Data

US 2013/0012893 A1    Jan. 10, 2013

Related U.S. Application Data

(60) Provisional application No. 61/501,671, filed on Jun. 27, 2011.

(51) Int. Cl.
| | | |
|---|---|---|
| *A61F 9/00* | (2006.01) | |
| *A61P 27/02* | (2006.01) | |
| *A61M 35/00* | (2006.01) | |
| *A61K 9/14* | (2006.01) | |
| *A61K 9/00* | (2006.01) | |
| *A61K 9/12* | (2006.01) | |

(52) U.S. Cl.
CPC ............... *A61K 9/0048* (2013.01); *A61K 9/12* (2013.01)

(58) Field of Classification Search
CPC ......... A61M 11/00; A61M 35/00; A61F 9/00; A61P 27/02; A61K 9/14
USPC .................................. 604/310, 290; 424/489
See application file for complete search history.

(56) References Cited

U.S. PATENT DOCUMENTS

| | | | |
|---|---|---|---|
| 3,995,635 A | | 12/1976 | Higuchi et al. |
| 4,241,877 A | * | 12/1980 | Hughes .................. 239/405 |
| 5,165,391 A | * | 11/1992 | Chiesi et al. ........... 128/200.23 |
| 5,458,135 A | * | 10/1995 | Patton et al. ........... 128/200.14 |
| 2001/0018916 A1 | | 9/2001 | Van Oort et al. |
| 2002/0036358 A1 | * | 3/2002 | Watkins ................... 261/26 |
| 2004/0140374 A1 | | 7/2004 | Snyder et al. |
| 2007/0119968 A1 | * | 5/2007 | Collins et al. ........... 239/102.1 |
| 2007/0158477 A1 | | 7/2007 | Wu et al. |
| 2008/0299049 A1 | | 12/2008 | Stangl |

OTHER PUBLICATIONS

International Search Report and Written Opinion mailed Nov. 7, 2012 for PCT Application No. PCT/US2012/044447, 13 pages.

* cited by examiner

*Primary Examiner* — Tatyana Zalukaeva
*Assistant Examiner* — Sara Sass
(74) *Attorney, Agent, or Firm* — Mintz Levin Cohn Ferris Glovsky and Popeo PC

(57) ABSTRACT

There is provided methods for administering a toroidal pharmaceutical composition to a subject. The method includes dispensing a toroidal pharmaceutical composition, and allowing the toroidal pharmaceutical composition to contact a target organ of the subject, thereby administering the toroidal pharmaceutical composition. There are additionally provided toroidal aerosol delivery systems.

19 Claims, 16 Drawing Sheets

Fig. 10A
Fig. 10B
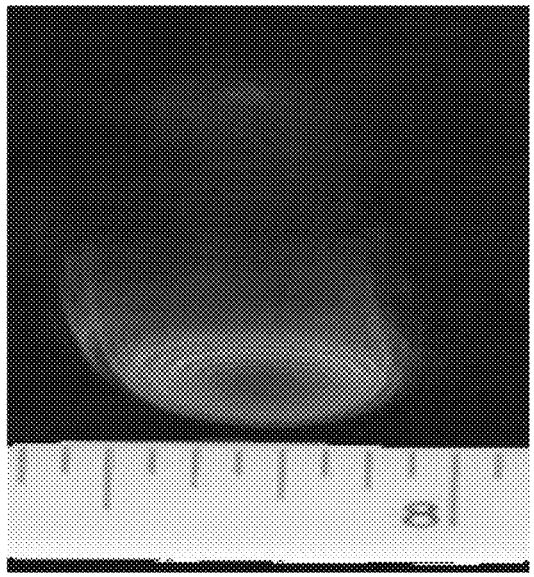
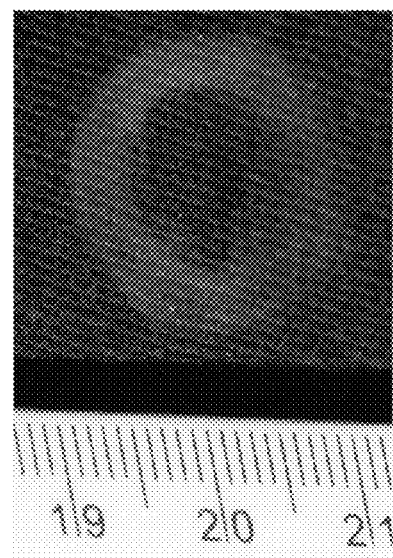
Fig. 11
Directional movement →
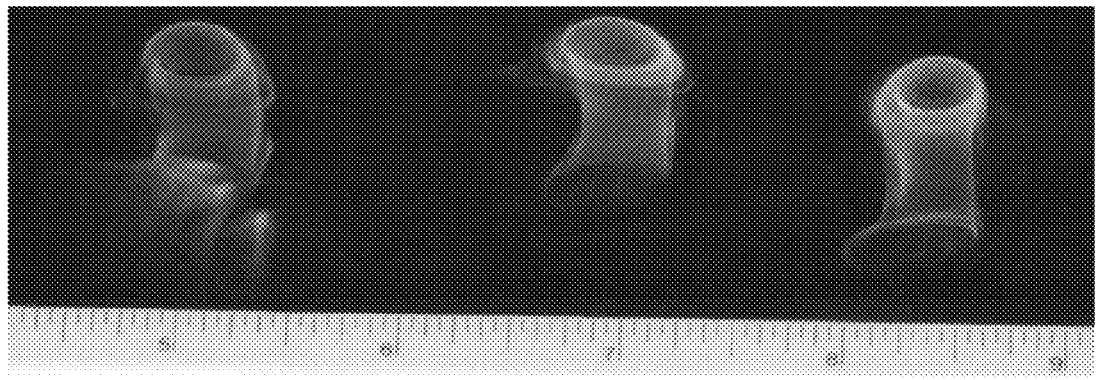

← Directional Movement

TOROIDAL PHARMACEUTICAL FORMULATIONS

CROSS-REFERENCES TO RELATED APPLICATIONS

This application claims the benefit of U.S. Provisional Application No. 61/501,671, filed Jun. 27, 2011, the entire contents of which is hereby incorporated by reference herein and for all purposes.

BACKGROUND OF THE INVENTION

Methods for administering therapeutic agents to a body organ (e.g., the eye) typically employ either drops (e.g., ocular drops) or an aerosol plume to administer the agents. Without wishing to be bound by any theory, it is believed that such forms of administration can be inaccurate and insufficient in mechanical delivery as well as retention of therapeutic agent at the targeted organ. For example, drops can provide a large quantity of liquid to the eye, beyond the volume capacity of the compartment, resulting in therapeutic agent loss, uncontrolled dose, rapid removal of drops, and uncomfortable administration. Moreover, instillation of an eye drop can be mechanically challenging maneuver for many individuals. For example, once the drop is instilled, blinking of the eyelashes can remove a large and variable volume of the drop. Finally the instillation of large volumes of liquids to the eye can stimulate lacrimal clearance. These factors can be avoided by the use of small volume controlled delivery of agents to the existing lacrimal fluid, as described herein, or to the surface of the target organ.

Regarding aerosol delivery to the eye, aerosol plume geometry can be difficult to control, and ensuring that the aerosol plume deposits on the eye surface can be problematic. Additionally, the force of the aerosol plume can be uncomfortable because in many cases the process of aerosolization is not decoupled from the process of administration to the eye, resulting in a rapidly moving aerosol plume. Accordingly, the use of aerosols emitted as a plume can have challenges associated with complexity of the plume geometry and mechanical coordination of the maneuvers associated with administration. Moreover, the direction and distance of the plume relative to the eye can have variable effects on the amount of therapeutic agent that arrives at the intended target.

Accordingly, there are provided herein inter alia devices and methods for delivering agents (e.g., therapeutic agents in the form of toroidal pharmaceutical composition) in approximately toroidal geometric units of volume suitable for administration of therapeutically active agent into a variety of organs, e.g., eye, ear, nose, throat and the like. There are additionally provided devices and methods for tuning (e.g., adjusting) the toroidal dimensions and aerosol characteristics of the administered therapeutic agents. There are additionally provided devices and methods for management of formulation to ensure appropriate dosing for a variety of therapeutically active agents.

BRIEF SUMMARY OF THE INVENTION

In a first aspect, there is provided a method for administering a toroidal pharmaceutical composition to a subject. The method includes dispensing a toroidal pharmaceutical composition from a toroidal aerosol delivery system, the toroidal pharmaceutical composition including an aerosolized therapeutic agent. The method further includes allowing the toroidal pharmaceutical composition to contact a target organ of the subject, thereby administering the toroidal pharmaceutical composition.

In another aspect, there is provided a toroidal aerosol delivery system for use in the methods described herein, which includes an aerosol chamber, an aerosol generator in fluid communication with the aerosol chamber, an orifice in fluid communication with the aerosol chamber, and an actuator in mechanical communication with the aerosol chamber.

In another aspect, there is provided a toroidal aerosol delivery system, including a gas reservoir chamber, an in-line aerosol generator adapted to deliver an aerosolized therapeutic agent, an orifice in fluid communication with the gas reservoir chamber and the in-line aerosol generator, the orifice adapted to emit a toroidal pharmaceutical composition, and an actuator in mechanical communication with the gas reservoir chamber.

In another aspect, there is provided a method for administering an ophthalmically active pharmaceutical ingredient to a subject in need thereof. The method includes administering an effective amount of a toroidal pharmaceutical composition to an eye of the subject, wherein the toroidal pharmaceutical composition includes the ophthalmically active pharmaceutical ingredient.

In another aspect, there is provided a toroidal pharmaceutical composition including an ophthalmically active pharmaceutical ingredient.

BRIEF DESCRIPTION OF THE DRAWINGS

FIGS. 1E-1G illustrate the "thickening" of the ring portion of the torus as the ring radius is increased while the major radius is kept constant, and FIGS. 1H-1J illustrate a corresponding "thinning" of the ring portion of the torus as the ring radius is decreased while the major radius is kept constant.

FIG. 10A depicts an exemplary toroidal pharmaceutical composition obtained via stroboscopic photography. FIG. 10B, depicts the toroidal pharmaceutical composition as viewed along the axis of propagation.

FIG. 11 depicts a pharmaceutical toroidal composition emitted from a device described herein and followed in time with stroboscopic flashes of known timing and duration.

FIG. 17. The figure depicts the results of particle sizing experiments using the Sympatec-HELOS device. See Example 7.

FIG. 18A: 0.05% fluorescein solution; FIG. 18B: 5.0% fluorescein solution.

DETAILED DESCRIPTION OF THE INVENTION

I. Definitions

Figure 1:
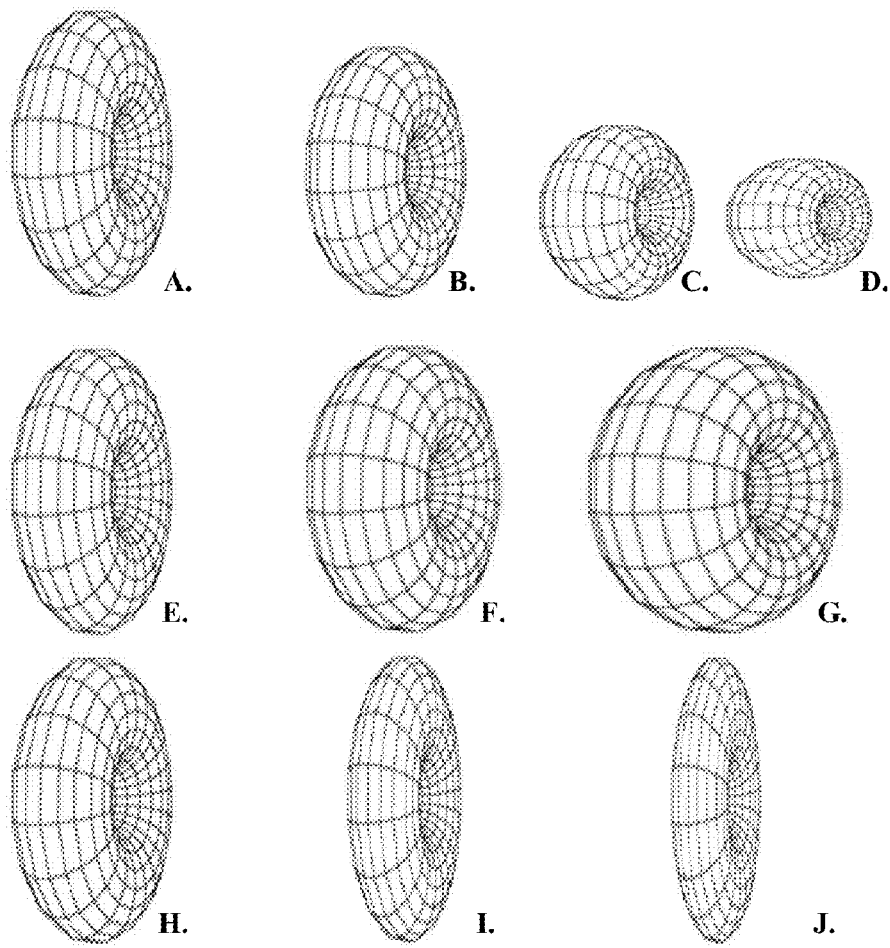
FIGS. 1A-1J depict exemplary tori useful for the methods and devices described herein. The series of tori in FIGS. 1A-1D illustrate the reduction in the overall size of a torus with reduction in the major radius of the torus.

The term "vortex" generally refers, as understood in the art, to a spinning fluid flow structure, e.g., a liquid, a gas, a gas including liquid or solid or particles entrained within, or the like. An understanding of the fluid dynamics of vortices, and in particular toroidal vortices, is provided in the literature, e.g., as cited herein. See e.g, Glezer, 1988, *Phys. Fluid* 31:3532-3542; Sullivan, et al., 2008, *J. Fluid Mech* 609:319-347; Haller, 2005, *J. Fluid Mech.* 525:1-26; Akhmetov, 2009, VORTEX RINGS, Springer Berlin Heidelberg; each of which is incorporated herein by reference in its entirety and for all purposes.

Exemplary vortices include free vortex (i.e., line vortex), forced vortex, hairpin vortex (e.g., horseshore vortex), laminar plate vortex, vortex ring (i.e., toroidal vortex), and the like. The terms "free vortex," "line vortex," "irrotational vortex" and the like refer to a vortex in a fluid wherein the tangential velocity of the fluid varies invertsely as the distance from the center of rotation. Conversely, "forced vortex," "rotational vortex" and the like refer to a vortex wherein fluid rotates as a solid body. The terms "hairpin vortex," "horseshoe vortex" and the like generally refer to a vortex system about a body (e.g., a wing) in motion relative to a fluid (e.g., air), as known in the art. The terms "vortex ring," "toroidal vortex" and the like refer to a region of rotating fluid characterized by a toroidal shape. The toroidal vortex may be moving through the same or a different fluid.

The term "vortex line" refers to a line at the core of a vortex about which every particle in the vortex can be considered to circulate. Vortex lines can begin and end at the boundary of the fluid forming the vortex, or vortex lines can form closed loops. Vortex lines which form closed loops characterize toroidal vortices. The term "vortex core" refers to the region of a vortex near the vortex line. It is understood that vortex lines can form in a variety of shapes, including generally circular, oval-shaped, pear-shaped, polygonal, and the like, as known in the art.

Without wishing to be bound by any theory, it is believed that fluid dynamics flow structures useful in the methods disclosed herein include toroidal vortices. Accordingly, the terms "toroidal pharmaceutical composition" and the like refer to an aerosol unit dosage of an aerosolized active pharmaceutical ingredient (i.e., a toroidal bolus of an aerosolized therapeutic agent) wherein at least a portion of the aerosol unit dosage is formed into the general shape of a torus or other similarly shaped vortex as described herein and known in the art. Thus, in some embodiments, a toroidal pharmaceutical composition is or contains a toroidal vortex or portion thereof, wherein the toroidal vortex or portion thereof includes an aerosolized active pharmaceutical ingredient (e.g., an ophthalmically active pharmaceutical ingredient). In some embodiments, the toroidal pharmaceutical composition is or includes a toroidal vortex that includes an aerosolized active pharmaceutical ingredient (e.g., an ophthalmically active pharmaceutical ingredient). It is understood that the methods and devices disclosed herein contemplate physical, i.e., non-idealized, flow structures including toroidal vortices. It is further understood that the coupling of a flow structure to the environment can cause change in the shape of the flow structure with time, e.g., as energy and/or angular momentum is transferred from the flow structure to the environment. A person having ordinary skill in the art will understand that where a toroidal pharmaceutical composition is administered using a device disclosed herein, it is meant that the aerosoal unit dosage when released from the device (e.g., the orifice) is a toroidal pharmaceutical composition. In some embodiments, the toroidal pharmaceutical composition is a toroidal pharmaceutical composition when contacting the target organ (e.g., the eye). Accordingly, the terms "general shape of a torus or other vortex" and the like refer to the general appearance of the flow structure, wherein the vortex (e.g., toroidal vortex including entrained particles) can change with time as it interacts with the environment. Exemplary modes of change in this context include, e.g., dispersion of matter from aspects of the vortex which are distal to the vortex core.

In some embodiments described herein, the toroidal pharmaceutical composition has or contains an aerosol unit dosage in the approximate shape of a torus. In some embodiments described herein, the aerosolized pharmaceutical composition includes liquid or solid particles suspended in gas, e.g., air, propellant, inert gas (e.g., $N_2$, $CO_2$, Ar and the like), and the like. Exemplary propellants include HFA 134a, HFA227ea, and a variety of liquified gases includes propane, butane, dimethylether, and the like. In some embodiments, the gas includes a propellant, as known in the art. In some embodiments, the gas includes air and a propellant. The aerosolized pharmaceutical composition can be heterogeneous or homogeneous, as known in the art.

The terms "pharmaceutical composition," "pharmaceutical ingredient," "therapeutic composition," "therapeutic agent" and the like refer to a composition generally considered as safe for administration to a subject for treatment or prevention of a disease or disorder. The terms "subject" and the like refer to a human or non-human animal, preferably a human. The terms "in need of treatment" and the like in the context of a subject refers, in the customary sense, to a perceived need for treatment in response to a disease or disorder. In some embodiments, the perceived need is the result of a diagnosis by a medical or veterinary practitioner. In some embodiments, a pharmaceutical composition includes a therapeutic agent, e.g., a drug. In some embodiments, a pharmaceutical composition additionally includes one or more excipients, e.g., buffer, flow agent, solubilizing agent, preservative, and the like, as known in the art.

The terms "effective amount" and the like in the context of administration of a toroidal pharmaceutical composition as described herein refer to an amount of an active pharmaceutical ingredient within the toroidal pharmaceutical composition which is effective to meet the needs of a subject in need of treatment. The term "active pharmaceutical ingredient" refers in the customary sense to a chemical composition (e.g., a drug) or a plurality of chemical compositions known in the art to be effective in the treatment of a disease or disorder. The terms "ophthalmically active pharmaceutical ingredient" refer to an active pharmaceutical ingredient known to be useful in the treatment of a disease or disorder of the eye. See e.g., PHYSICIANS' DESK REFERENCE®, 2012, PDR Network, LLC, Chestertown, Md.). In one embodiment, the active pharmaceutical ingredient is an ophthalmically active pharmaceutical ingredient. In one embodiment, the need of the subject is treatment of an ophthalmic disease. Amounts of active pharmaceutical ingredients, and in particular ophthalmic active pharmaceutical ingredients, are well known in the art.

The terms "toroidal aerosol delivery system" and the like refer to a system as described herein capable of dispensing a toroidal pharmaceutical composition. In some embodiments, the toroidal aerosol delivery system can be tuned as described herein. The terms "tune" and the like in the context of a toroidal aerosol delivery system refer to modulation or adjustment of the physical characteristics, e.g., size, rotational velocity, linear velocity, and the like of a toroidal pharmaceutical composition. The terms "charged toroidal aerosol delivery system" and the like refer to a toroidal aerosol delivery system containing an agent (e.g., aerosolized therapeutic agent) ready for dispensing.

The term "aerosol generator" refers to a device that generates fine solid particles or liquid droplets of pharmaceutically active ingredients to a gas vehicle. In some embodiments, the gas vehicle is present within a gas chamber. In such embodiments, the aerosol generator may be in fluid communication with the gas chamber in order to enable the formation of an aerosolized pharmaceutically active ingredient within the gas chamber upon delivery of the fine solid particles or liquid droplets of pharmaceutically active ingredients from the aerosol generator.

In one embodiment, the toroidal aerosol delivery system includes an in-line aerosol generator. The terms "in-line aerosol generator" and the like refer to aerosol generators adapted for delivering (e.g., controlled emission of) aerosolized therapeutic agent directly to an orifice of a device disclosed herein. In some embodiments, the toroidal aerosol delivery system including an in-line aerosol generator can be tuned as described herein. The in-line aerosol generator is typically in fluid communication with the orifice of the devices described herein such that the aerosolized therapeutic agent is delivered to a gas vehicle as the gas vehicle exits the orifice thereby forming a toroidal pharmaceutical formulation. Exemplary in-line aerosol generators include evaporation/condensation devices which are useful, e.g., for emission of particles with known sizes. Additional in-line aerosol generators includes heating/cooling elements, e.g., wire filament (heating) or Peltier plates (cooling) to alter gaseous media density thereby altering the aerodynamics and stability of an aerosol or plume. In one embodiment, the in-line aerosol generator is a filament coated with therapeutic agent, which therapeutic agent aerosolizes upon heating of the filament. It is understood that modulation of liquid viscosity can also influence particle size generation. In another embodiment, an in-line aerosol generator includes a light source for photoconversion of a therapeutic agent, or for initiation of polymerization to aid in the formation of particulates once dispersed as an aerosol. In one embodiment, the in-line aerosol generator includes a plurality of orifices (e.g., jet nozzles) which direct the therapeutic agent into a toroidal bolus as it passed the in-line aerosol generator.

The terms "actuate" and the like, in the context of methods and devices described herein, refer to a causative action that produces a toroidal pharmaceutical composition, e.g., by pushing a button or otherwise applying energy. In one embodiment, actuation provides energy to the toroidal aerosol delivery system, thereby transiently increasing the pressure within the toroidal aerosol delivery system, resulting in emission of a toroidal pharmaceutical composition. In one embodiment, energizing the actuator refers to application of a force (e.g., mechanical, electromechanical, vibration, heat, and the like) to the aerosol chamber. In one embodiment, the force is provided by a propellant (e.g., compressed gas) upon the opening of a valve (e.g., a metering valve). In one embodiment, actuation is achieved with an electromechanical actuator, as known in the art. In one embodiment, actuation is achieved by energizing an aerosol generator, e.g., a vibration mesh ultrasonic nebulizer, vaporizer, and the like, whereby sufficient energy is imparted to transiently increase the pressure within the toroidal aerosol delivery system, resulting in emission of a toroidal pharmaceutical composition.

The term "fluid communication" refers in the customary sense to physical communication of a liquid or gas, typically between elements of a device.

The terms "administering" and the like refer, in the customary sense, to application of a substance, e.g., a therapeutic agent.

A "target organ" refers to an organ of a subject (e.g., an animal subject such as a mammalian subject including humans). A target organ may be an external organ or an internal organ (e.g., where the toroidal pharmaceutical composition is administered during surgery). Target organs include, for example, the eye, ear, nose and throat, as well as areas surrouding the eye, ear, nose and throat.

II. Theory of Tori

Toroidal Shapes.

Each of the terms "toroid", "torus," "tori," "toroidal" is used herein (e.g., in the context of a toroidal pharmaceutical composition) according to its plain meaning as used in the art. Specifically, the general shape of a toroid approximately resembles that of a doughnut shaped object, e.g., a surface obtained by revolving a general shape (e.g., a circle, oval and the like) in three dimensional space about an axis of revolution coplanar with the general shape. In the general case and as used herein, the distance from the general shape to the axis of revolution may not be constant during the revolution about the axis. Accordingly, tori contemplated herein include circular tori (i.e., having a constant distance during the revolution), and other tori (e.g., oval shaped, pear-shaped, and the like), which reflect a non-constant distance from the general shape to the axis of revolution during formation of the tori. In some embodiments, the distance from the general shape to the axis of revolution is approximately constant during the revolution about the axis. In some embodiments, the toroid is circular or approximately circular (e.g., an O-ring or the ring form of a solenoid).

In some embodiments, the axis of revolution does not touch the general shape, giving rise to a so-called "ring torus" (e.g., O-ring or doughnut having an open space therewithin). In some contexts, the axis of revolution is tangent to the general shape, giving rise to a so-called "horn torus." In some contexts, the axis of revolution transsects the general shape, giving rise to a so-called "spindle torus." It is expressly contemplated that in some embodiments the toroidal pharmaceutical compositions described herein can resemble the shape of a portion of a torus (e.g., a ring torus), i.e., having the approximate shape of a surface of revolution wherein the degree of revolution is through less than $2\pi$ radians, e.g., $\pi/2$ radians (quarter-torus), $\pi$ radians (half-torus), and the like. As further known in the art, additional types of torus obtain depending on the relative orientation of the axis of revolution and the general shape, e.g., horn torus, spindle torus, sphere, ellipsoid, and the like. Unless indicated otherwise, reference herein in the context of methods and devices described herein to "torus," "tori," "toroidal" and the like refers to a ring torus and portions thereof, having real world examples including doughnut, inner tube, ring lifebuoy, O-ring, the toroidal boli described herein, and the like. As used herein, the terms "major radius," "major toroidal radius," "height of the torus" and the like refer to the radius about the axis of revolution, thus describing the overall size of the tori. The terms "ring radius," "ring toroidal radius," "ring thickness," "width of the torus" and the like refer to the radius of the general shape, thus describing the overall size and shape of the ring forming the torus. It is understood that if the general shape is a non-circular ellipse, then the general shape can be mathematically described by a plurality of radii, e.g., major elliptical radius, minor elliptical radius, and the like. Notwithstanding such mathematical description of an ideal torus, absent express indication otherwise, the terms "ring radius," "ring toroidal radius," "ring thickness" and the like as used herein describe the general size and/or shape of the ring forming the torus.

Exemplary tori useful in the methods and devices described herein include those illustrated in FIGS. 1A-1J. The series of tori in FIGS. 1A-1D illustrate the reduction in the overall size of a torus with reduction in the major radius of the torus. FIGS. 1E-1G illustrate the "thickening" of the ring portion of the torus as the ring radius is increased while the major radius is kept constant, and FIGS. 1H-1J illustrate a corresponding "thinning" of the ring portion of the torus as the ring radius is decreased while the major radius is kept constant.

Figure 2:
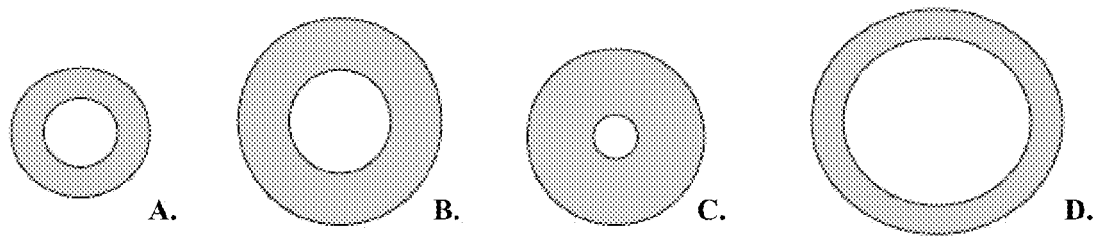
FIGS. 2A-2D illustrate various tori as viewed along the axis of revolution.
Figure 3:
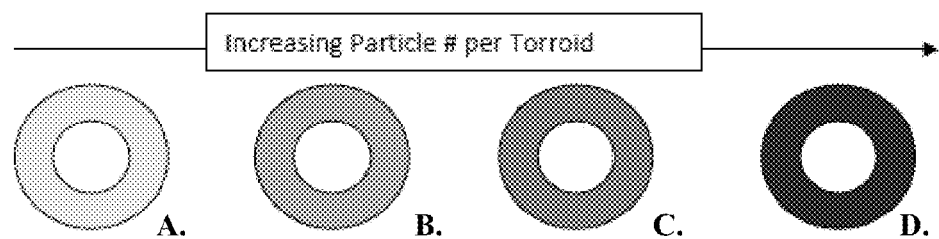
FIG. 3A-3D depict tori of equivalent major toroidal radius and equivalent ring toroidal radius having increasing amounts (order FIGS. 3A-3D, least to greatest) of aerosolized agent as the density of particles (i.e., number of particles per unit volume) within the aerosolized agent is increased. Legend: light gray to black: least to greatest concentration of particles per toroid.

As illustrated in FIG. 2, modulation of the major toroidal radius and ring toroidal radius provides a method for modulating the overall size of the toroidal bolus of aerosolized therapeutic agent (i.e., toroidal pharmaceutical composition) impinging on the target organ. FIGS. 2A-2D illustrate exemplary tori as viewed along the axis of revolution, which is also the axis of propagation.

As known in the art, the volume of an ideal circular torus (i.e., ring torus having a circle rotated about an axis of revolution) can be mathematically described as $$V = 2\pi^2 R r^2 \quad \text{(Eqn. 1)}$$

where "R" is the distance from the axis of revolution to the center of the circle forming the ring portion of the torus, and "r" is the radius of the ring portion (e.g., circular body) of the torus. As commonly used in the art, the ratio of major toroidal radius to ring toroidal radius is the so-called "aspect ratio" of a torus. In some embodiments, the torus produced herein approximately obeys Eqn. 1. Thus, in some embodiments, the toroidal pharmaceutical composition is or includes a toroidal vortex that can be approximately described by Eq. 1 that includes an aerosolized active pharmaceutical ingredient. In some embodiments, the toroidal pharmaceutical composition is or includes a toroidal vortex that can be described by Eq. 1 that includes an aerosolized active pharmaceutical ingredient.

Aerosol Density.

By modulating the density of an aerosolized therapeutic agent within a toroidal pharmaceutical composition (also referred to herein as a "toroidal bolus") as described herein (e.g., number of particles/unit volume), the amount of aerosolized therapeutic agent delivered in the toroidal pharmaceutical composition (toroidal bolus) can be varied. For example, as shown in FIG. 3A-3D, tori of equivalent major toroidal radius and equivalent ring toroidal radius provide increasing amounts of aerosolized therapeutic agent as the density of particles within the aerosolized therapeutic agent is increased.

Thus, modulating the height of the torus (i.e., major toroidal radius) and thickness of the ring portion of the torus (i.e., ring toroidal radius) allows for different volumes of an aerosol forming the torus to be emitted by the devices described herein. Such modulation has a direct effect on the volume and surface area of the resultant torus, allowing for tunable deposition of drug contained within the aerosol to be deposited on the target organ.

Mechanics of Toroid Propagation.

Figure 4:
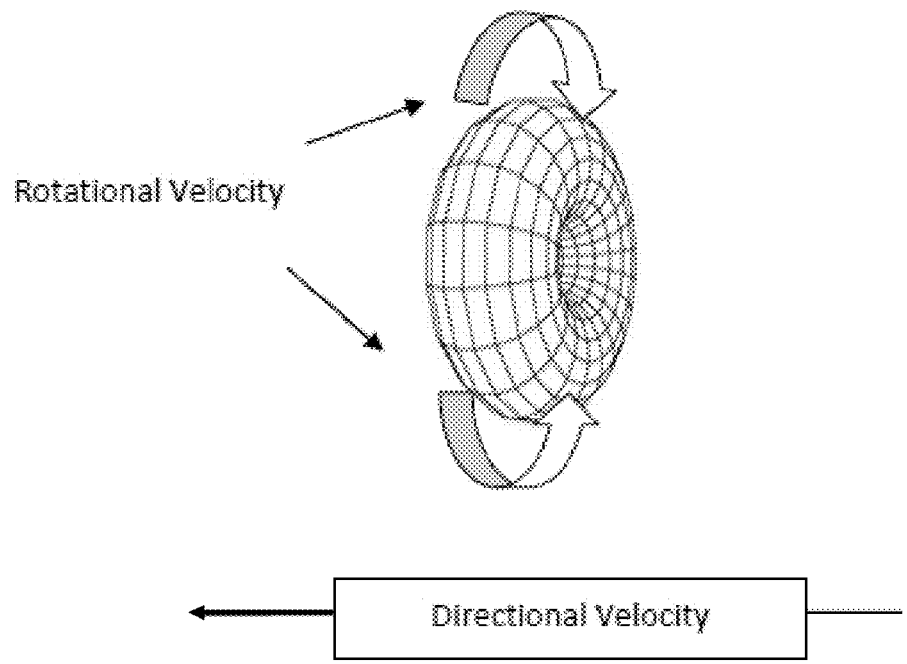
FIG. 4 depicts rotational velocity and directional velocity in exemplary tori, which are different parameters characterizing the mechanics of toroid propagation.

Without wishing to be bound by any theory, it is believed that the velocity of propagation of a toroid bolus in three-dimensions can be modulated. The toroidal boli described herein include particles (i.e., aerosolized therapeutic agent) entrained in a moving gaseous media. At least two parameters that relate to the transport of the aerosolized therapeutic agent can be controlled. Firstly, the directional velocity, i.e., the rate that the torus as a whole travels, can be modulated. Secondly, the internal rotational velocity of the toroid can be modulated (e.g., by modulating the mechanical force and/or orifice size as described below). These two velocity components can be controlled to modulate inertial characteristics of the entrained particles. For example, a toroid can be emitted moving very slowly forward while having high rotational velocity or vice versa. As depicted in FIG. 4, rotational velocity and directional velocity are different parameters characterizing the mechanics of toroid propagation. Theoretical treatments from the field of flow dynamics on the mechanics of vortex propagation including toroidal vortices (e.g., toroidal pharmaceutical compositions as disclosed herein) are are known in the art and include, e.g., Glezer, 1988, Id.; Sullivan, et al., 2008, Id.; Haller, 2005, Id.; and Akhmetov, 2009, Id.

III. Methods

There are provided methods and devices for the ordered control and accurate transmission (i.e., administration to a subject in need thereof) of agents (e.g., therapeutic agents) entrained within a flow structure (e.g., a toroidal bolus). Contemplated agents include medicaments for the treating of a disease or disorder, prophylactic agents for the prevention of a disease or disorder, biological agents (e.g., vaccines, gene therapy vectors, and the like), non-biological vaccines and gene therapy vectors, particles facilitating controlled release and/or enhanced retention of therapeutic agents, nutritional supplements, and diagnostic reagents.

Exemplary applications (e.g., in the context of ophthalmic treatment) for the devices and methods disclosed herein include, in one embodiment, the case where a small therapeutic window is available for a therapeutic agent. The term "therapeutical window" refers, as customary in the art, to a range of dosing of a therapeutic agent which can effectively treat a disease or disorder while staying within the safety range established for the therapeutic agent. Methods for establishing safety ranges are well known in the art. In one embodiment, the therapeutic agent is highly potent and/or toxic, necessitating very low dosing. In one embodiment, systemic exposure of the therapeutic agent via the lacrimal duct is beneficially avoided. In one embodiment, the risk for cross-contamination or re-infection is high, e.g., microbial infection, and use of the devices and methods disclosed herein mitigates such risk, e.g., by avoiding direct physical communication of the disclosed device with the target organ. In one embodiment, the subject is physically incapable of administering therapeutic agent by conventional methods (e.g., drops) due to lack of physical co-ordination (e.g., pediatric, neonatal, comatose, senile, elderly, physically handicapped, and the like). In a further embodiment, the subject lacks the ability to blink, thereby compromising regulated clearance. Moreover, in one embodiment, the relatively small size of the toroidal bolus is beneficial to avoid wetting the area surrounding the target (e.g., in ocular surgury). In one embodiment, treatment is directed to excessively watery eyes, as known in the art. In one embodiment, a subject is sensitive to preservatives, and the use of preservatives is beneficially avoided without compromising long term storage of therapeutic agent.

In a first aspect, there is provided a method for administering a toroidal pharmaceutical composition to a subject. The method includes dispensing a toroidal pharmaceutical composition from a toroidal aerosol delivery system, the toroidal pharmaceutical composition including an aerosolized therapeutic agent. The method further includes allowing the toroidal pharmaceutical composition to contact a target organ of the subject, thereby administering the toroidal pharmaceutical composition. In one embodiment, the subject is in need of prevention or treatment for a disease or disorder.

In one embodiment, the toroidal pharmaceutical composition assumes a shape resembling a ring torus. In one embodiment, the toroidal pharmaceutical composition assumes a shape resembling a horn torus. In one embodiment, the toroidal pharmaceutical composition assumes a shape resembling a spindle torus. In one embodiment, the toroidal pharmaceutical composition assumes a shape resembling a portion of a ring torus, e.g., a half torus, a quarter torus, and the like.

In one embodiment, the toroidal pharmaceutical composition includes an agent, e.g., a therapeutic agent. In one embodiment, the therapeutic agent is a drug. In one embodiment, the therapeutic agent is a plurality of drugs.

In one embodiment, the toroidal aerosol delivery system includes an aerosol chamber, an aerosol generator in fluid communication with the aerosol chamber, the aerosol generator adapted to charge the aerosol chamber with the aerosolized therapeutic agent, an orifice in fluid communication with the aerosol chamber, the orifice adapted to emit the toroidal pharmaceutical composition; and an actuator in mechanical communication with said aerosol chamber.

In some embodiments, the dispensing is accomplished using a toroidal aerosol delivery system, e.g., a tunable pulsed toroidal aerosol delivery system. In some embodiments, the toroidal aerosol delivery system is tunable. In some embodiments, the toroidal aerosol delivery system provides pulsed delivery of toroidal pharmaceutical composition. In some embodiments, the toroidal aerosol delivery system is a tunable pulsed toroidal aerosol delivery system. The term "tunable pulsed toroidal aerosol delivery system" refers to a toroidal aerosol delivery system which can be tuned, as described herein, and which provides pulsed delivery of a toroidal pharmaceutical composition. In some embodiments, dispensing is performed in proximity to the target organ. The proximity to the target organ is dependent on the particular organ, e.g., size, accessibility, and the like. For example, for dispensing to the eye, the toroidal aerosol delivery system can be 1, 2, 3, 4, 5, 6, 7, 8, 9, 10, 12, 14, 16, 18, 20 cm, or even further from the eye. For the throat, the toroidal aerosol delivery system can be 1, 2, 3, 4, 5, 6, 7, 8, 9, 10, 15, 20, 25, 30, 35, 40, 45, 50 cm, or even further from the throat. For the nose, the toroidal aerosol delivery system can be 1, 2, 3, 4, 5, 6, 7, 8, 9, 10 cm, or even further from the nose. For the ear, the toroidal aerosol delivery system can be 1, 2, 3, 4, 5, 6, 7, 8, 9, 10 cm, or even further from the ear.

In some embodiments, allowing the toroidal pharmaceutical composition to contact a target organ includes allowing a generally toroid-shaped bolus of an aerosolized therapeutic agent to contact the target organ.

In some embodiments, administering refers to instilling a pharmaceutical composition, in the form of a toroidal pharmaceutical composition, at the eye. In some embodiments, administering refers to topical administration to an organ, e.g., ear, nose, throat, bronchus, skin and the like.

In some embodiments, dispensing is accomplished by charging a toroidal aerosol delivery system with a therapeutic agent, thereby forming a charged toroidal aerosol delivery system. In some embodiments, the charged toroidal aerosol delivery system is a charged tunable pulsed toroidal aerosol delivery system.

In some embodiments, actuating is accomplished by mechanical manipulation of an actuator, thereby providing a transient increase in the pressure of the aerosolized therapeutic agent with an aerosol chamber.

In some embodiments, the toroidal aerosol delivery system includes an aerosol chamber, an aerosol generator in fluid communication with the aerosol chamber, which aerosol generator is adapted to charge the aerosol chamber with an aerosolized therapeutic agent, an orifice in fluid communication with the aerosol chamber, which orifice is adapted to emit a toroidal bolus of an aerosolized therapeutic agent as a toroidal pharmaceutical composition, and an actuator in mechanical communication with said aerosol chamber. In some embodiments, the toroidal pharmaceutical composition resembles a ring torus. In some embodiments, the toroidal pharmaceutical composition resembles a portion of a ring torus. In some embodiments, the orifice is circular. In some embodiments, the orifice is not circular, e.g., square, rectangular, triangular, star-shaped, half-circular, and the like.

In some embodiments, charging is accomplished by delivering a non-aerosolized therapeutic agent into the aerosol generator and allowing the aerosol generator to produce the aerosolized therapeutic agent from the non-aerosolized therapeutic agent, and delivering the aerosolized therapeutic agent to the aerosol chamber, thereby charging the charged toroidal aerosol delivery system; e.g., charged tunable pulsed toroidal aerosol delivery system. In some embodiments, charging fills the entire aerosol chamber with aerosolized therapeutic agent. In some embodiments, charging fills a portion, e.g., the bottom portion, of the aerosol chamber with aerosolized therapeutic agent. In some embodiments, the aerosol chamber further includes a baffle adapted to facilitate charging of only a portion of the aerosol chamber.

In some embodiments, actuating is accomplished by energizing the actuator. In some embodiments, the actuator is energized by application of a mechanical force. In some embodiments, the energizing produces a transient increase in the pressure within the aerosol chamber, which results in emission of the toroidal pharmaceutical composition through the orifice of the aerosol chamber. In some embodiments, the actuator is energized by application of an electrical or electromechanical force. In some embodiments, the actuator is energized by the opening of a valve to release a pressurized gas, e.g., a propellant as discussed herein. In one embodiment, actuation is achieved by energizing an aerosol generator, e.g., a vibration mesh ultrasonic nebulizer, vaporizer, and the like, whereby sufficient energy is imparted to transiently increase the pressure within the aerosol chamber, resulting in emission of a toroidal pharmaceutical composition.

In some embodiments, the application of mechanical force is adapted in combination with the orifice size and the volume of the aerosol chamber to modulate (i.e., tune) one or more of toroidal size, toroidal velocity, or directional velocity of the resulting toroidal pharmaceutical composition emitted through the orifice. For example, application of an appropriate force to the aerosol chamber (i.e., energizing) in combination with appropriate orifice size can produce a toroidal pharmaceutical composition having a height (i.e., extent impinging on a target organ) of e.g., 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 4.0, 5.0 cm, or even greater. In some embodiments, the target organ is the eye, and the extent (i.e., height) of the toroidal pharmaceutical composition (i.e., toroidal bolus of aerosolized therapeutic agent) is less than the width of the eye, e.g., 0.1, 0.2, 0.3, 0.4, 0.5, 0.6, 0.7, 0.8, 0.9, 1.0, 1.2, 1.4, 1.6, 1.8, 2.0 cm, or even greater. It is understood that by providing a toroidal pharmaceutical composition with largest extent less than the width of the eye, most of the therapeutic agent within the toroidal bolus will enter the eye and not be lost on the skin surrounding the eye.

Without wishing to be bound by any theory, it is believed that a more dense toroidal pharmaceutical composition is produced if the aerosol chamber is foreshortened. Accordingly, in some embodiments, the aerosol chamber is shorter in the direction of propagation of the toroidal pharmaceutical composition to achieve a more dense composition. Moreover, it is believed that higher toroidal rotational velocity of the toroidal pharmaceutical composition serves to keep the shape of the toroidal pharmaceutical composition intact during transit to the target organ. Accordingly, application of an initial rapid impulse (i.e., high initial force) during actuation results in a higher toroidal rotational velocity. Moreover, it is believed that the directional velocity of the toroidal pharmaceutical composition after emission from the orifice depends on the total impulse (i.e., integrated force over time) delivered during energizing of the aerosol chamber.

Accordingly, in some embodiments, the toroidal pharmaceutical composition is substantially intact upon contacting the target organ. The term "substantially intact" in this context means that there has been insubstantial loss of aerosolized therapeutic agent during the transit from the orifice of a device described herein to the target organ. For example, a substantially intact toroidal pharmaceutical composition can transport 50%, 60%, 70%, 80%, 90%, 92%, 94%, 96%, 98%, 99% or even greater percentage of aerosolized therapeutic agent to the target organ.

In one embodiment, the dispensing is accomplished using a toroidal aerosol delivery system. In some embodiments, the toroidal aerosol delivery system is tunable. In some embodiments, the toroidal aerosol delivery system provides pulsed delivery of toroidal pharmaceutical composition. In some embodiments, dispensing is performed in proximity to the target organ. The proximity to the target organ is dependent on the particular organ, e.g., size, accessibility, and the like. For example, for dispensing to the eye, the toroidal aerosol delivery system can be 1, 2, 3, 4, 5, 6, 7, 8, 9, 10, 12, 14, 16, 18, 20 cm, or even further from the eye. For the throat, the toroidal aerosol delivery system can be 1, 2, 3, 4, 5, 6, 7, 8, 9, 10, 15, 20, 25, 30, 35, 40, 45, 50 cm, or even further from the throat. For the nose, the toroidal aerosol delivery system can be 1, 2, 3, 4, 5, 6, 7, 8, 9, 10 cm, or even further from the nose. For the ear, the toroidal aerosol delivery system can be 1, 2, 3, 4, 5, 6, 7, 8, 9, 10 cm, or even further from the ear.

In some embodiments, dispensing is accomplished by charging a toroidal aerosol delivery system with a therapeutic agent, thereby forming a charged toroidal aerosol delivery system. In one embodiment, charging a toroidal aerosol delivery system refers to delivering a non-aerosolized therapeutic agent into the aerosol generator and allowing the aerosol generator to produce the aerosolized therapeutic agent. In one embodiment, charging a toroidal aerosol delivery system refers to loading an in-line aerosol generator with a therapeutic agent, e.g., providing a filament coated with a therapeutic agent.

In one embodiment, actuating is accomplished by mechanical manipulation of an actuator, thereby providing a transient increase in the pressure of the aerosolized therapeutic agent with an aerosol chamber. In one embodiment, actuating further includes providing mechanical or electronic energy to an in-line aerosol generator, thereby allowing aerosolization of a therapeutic agent.

In one embodiment, the target organ is the eye, ear, nose, or throat. In one embodiment, the target organ is an eye. In one embodiment, the subject is a mammalian subject. In one embodiment, the subject is a human subject.

In one embodiment, the toroidal aerosol delivery system includes a gas reservoir chamber, an in-line aerosol generator in fluid communication with the aerosol chamber, wherein the in-line aerosol generator is adapted to aerosolize a therapeutic agent, an orifice in fluid communication with the in-line aerosol chamber and in mechanical or electrical communication with the in-line aerosol generator, and an actuator in mechanical communication with the gas reservoir chamber and in mechanical or electrical communication with the in-line aerosol generator.

In one embodiment, the actuator includes a plurality of actuators, the plurality of actuators including a first actuator in mechanical communication with the gas reservoir chamber and a second actuator in mechanical or electrical communication with the in-line aerosol generator. In one embodiment, the actuator is further in mechanical or electrical communication with the in-line aerosol generator.

In one embodiment, charging is accomplished by delivering a non-aerosolized therapeutic agent into the in-line aerosol generator and allowing the in-line aerosol generator to produce the aerosolized therapeutic agent from the non-aerosolized therapeutic agent. In one embodiment, charging is accomplished by coating a filament included within the in-line aerosol generator.

In one embodiment, actuating is accomplished by energizing the actuator. In some embodiments, the actuator is energized by application of a mechanical force. In some embodiments, the energizing produces a transient increase in the pressure within the gas reservoir chamber, which results in emission of a toroidal bolus through the orifice of the gas reservoir chamber. In one embodiment, the in-line aerosol generator delivers aerosolized therapeutic agent into the toroidal bolus. In some embodiments, the actuator is energized by application of an electrical or electromechanical force. In some embodiments, the actuator is energized by the opening of a valve to release a pressurized gas, e.g., a propellant as discussed herein.

In one embodiment, the application of mechanical force is adapted in combination with the orifice size and the volume of the gas reservoir chamber to modulate (i.e., tune) one or more of toroidal size, toroidal velocity, or directional velocity of the resulting toroidal pharmaceutical composition emitted through the orifice. For example, application of an appropriate force to the aerosol chamber (i.e., energizing) in combination with appropriate orifice size can produce a toroidal pharmaceutical composition having a height (i.e., extent impinging on a target organ) of e.g., 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 4.0, 5.0 cm, or even greater. In some embodiments, the target organ is the eye, and the extent (i.e., height) of the toroidal pharmaceutical composition (i.e., toroidal bolus of aerosolized therapeutic agent) is less than the width of the eye, e.g., 0.1, 0.2, 0.3, 0.4, 0.5, 0.6, 0.7, 0.8, 0.9, 1.0, 1.2, 1.4, 1.6, 1.8, 2.0 cm, or even greater.

In one embodiment, actuating includes energizing the actuator. In one embodiment, energizing includes applying a mechanical force to the actuator. In one embodiment, the pressure within the aerosol chamber increases as a result of the energizing. In one embodiment, actuating including energizing the first actuator and the second actuator as disclosed herein. In one embodiment, the toroidal pharmaceutical composition is substantially intact upon contacting the target organ. In one embodiment, the target organ is the eye, ear, nose, or throat. In one embodiment, the target organ is an eye. In one embodiment, the subject is mammalian subject. In one embodiment, the subject is a human subject.

Without wishing to be bound by any theory, it is believed that a more dense toroidal pharmaceutical composition is produced if the gas reservoir chamber is foreshortened. Accordingly, in some embodiments, the gas reservoir chamber is shorter in the direction of propagation of the toroidal pharmaceutical composition to achieve a more dense composition.

In another aspect, there is provided a method for administering an aerosolized ophthalmically active pharmaceutical ingredient to a subject in need thereof. The method includes administering an effective amount of a toroidal pharmaceutical composition to an eye of the subject, wherein the toroidal pharmaceutical composition includes the aerosolized ophthalmically active pharmaceutical ingredient. In one embodiment, the subject is a mammalian subject. In one embodiment, the subject is a human subject. The terms "aerosolized ophthalmically active pharmaceutical ingredient" and the like refer, in the customary sense, to an aerosolized pharmaceutical ingredient beneficial for treatment of a disease or disorder of the eye, as known in the art.

In one embodiment, administering includes charging a toroidal aerosol delivery system, thereby providing a charged toroidal aerosol delivery system; and actuating the toroidal aerosol delivery system.

In one embodiment, the toroidal aerosol delivery system includes an aerosol chamber, an aerosol generator in fluid communication with the aerosol chamber, the aerosol generator adapted to charge the aerosol chamber with the aerosolized ophthalmically active pharmaceutical ingredient, an orifice in fluid communication with the aerosol chamber, the orifice adapted to emit the toroidal pharmaceutical composition, and an actuator in mechanical communication with the aerosol chamber.

In one embodiment, the toroidal aerosol delivery system includes a gas reservoir chamber, an in-line aerosol generator adapted to deliver the aerosolized ophthalmically active pharmaceutical ingredient, an orifice in fluid communication with the gas reservoir chamber and the in-line aerosol generator, the orifice adapted to emit the toroidal pharmaceutical composition, and an actuator in mechanical communication with the gas reservoir chamber.

IV. Devices

In another aspect, there is provided a toroidal aerosol delivery system for use in the methods described herein, which includes an aerosol chamber, an aerosol generator in fluid communication with the aerosol chamber, an orifice in fluid communication with the aerosol chamber, and an actuator in mechanical communication with the aerosol chamber. In some embodiments, the toroidal aerosol delivery system is a tunable pulsed toroidal aerosol delivery system as described herein. In one embodiment, the aerosol generator is adapted to charge the aerosol chamber with an aerosolized therapeutic agent.

Figure 5:
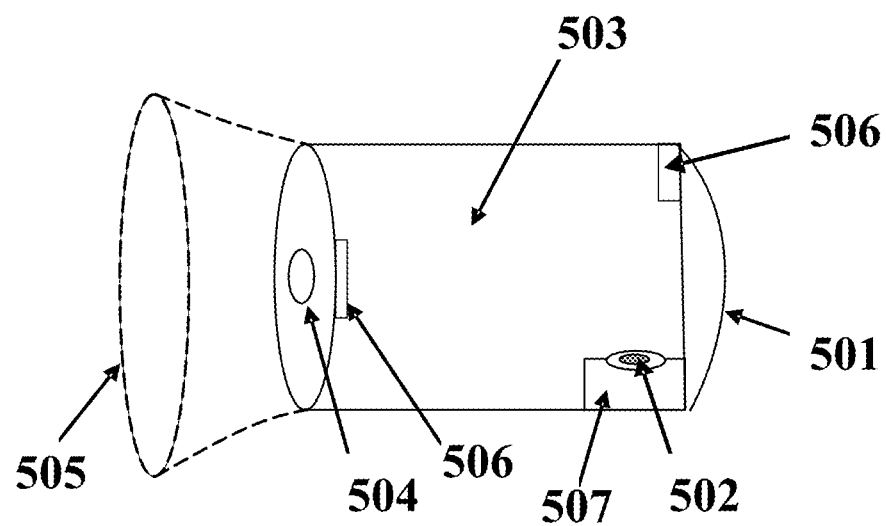
FIG. 5 depicts an exemplary toroidal aerosol delivery system as described herein.
Figure 6A:
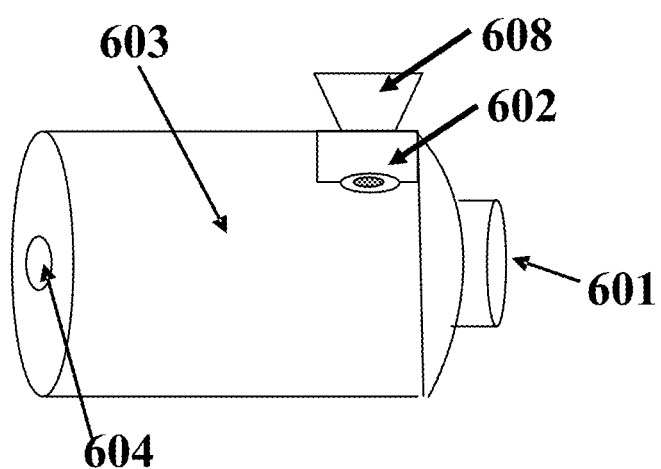
FIG. 6A depicts an exemplary toroidal aerosol delivery system as described herein, additionally having an external port 608 through which therapeutic agent can be introduced prior to aerosolization.
Figure 6B:
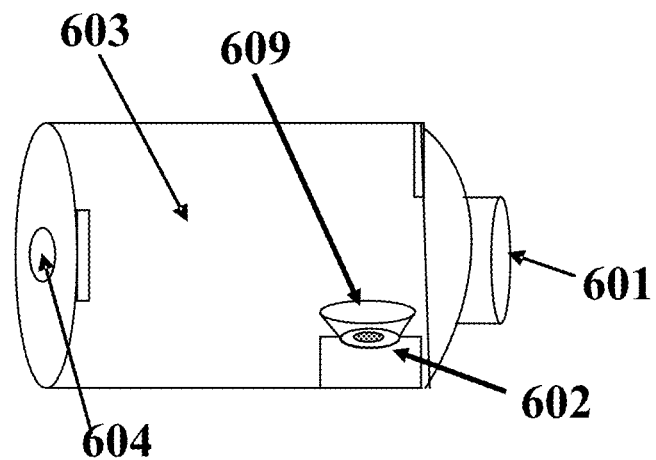
FIG. 6B depicts an exemplary toroidal aerosol delivery system as described herein, additionally having a dose loading feature 609 internal to aerosol chamber 603.
Figure 6C:
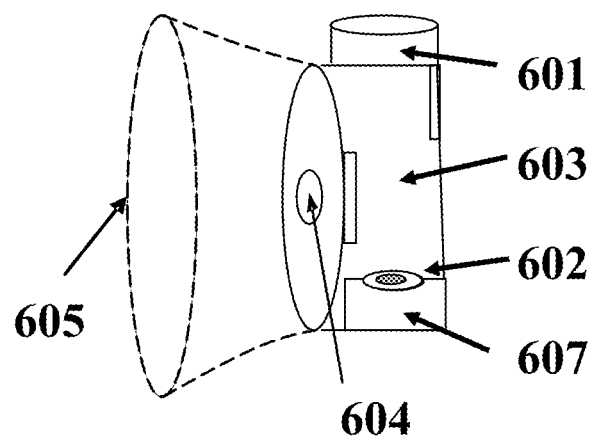
FIG. 6C depicts an exemplary toroidal aerosol delivery system as described herein, additionally including a metering dose button 610 affixed to the body of the aerosol chamber and in fluid communication with it.
Figure 7A:
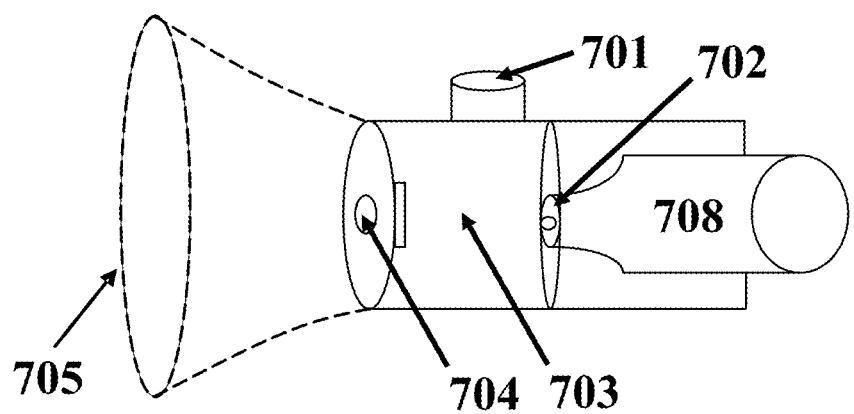
FIG. 7A depicts an exemplary toroidal aerosol delivery system as described herein, having a pressurized cannister containing therapeutic agent, excipients and/or propellant.
Figure 7B:
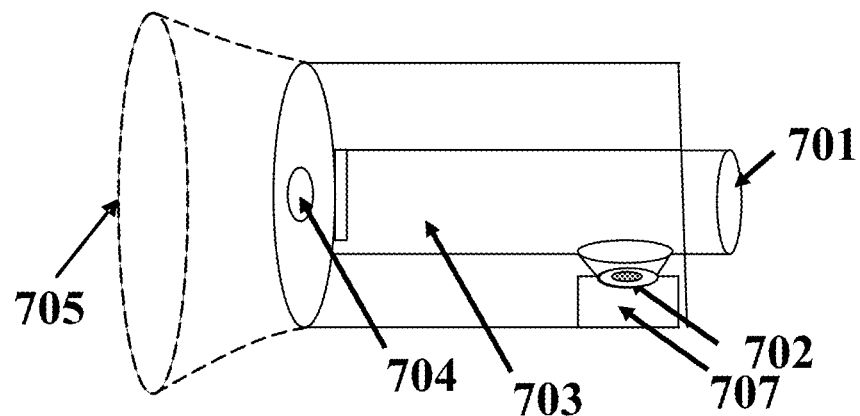
FIG. 7B depicts another embodiment wherein the volume of the aerosol chamber is reduced relative to that depicted in FIG. 7A.
Figure 8:
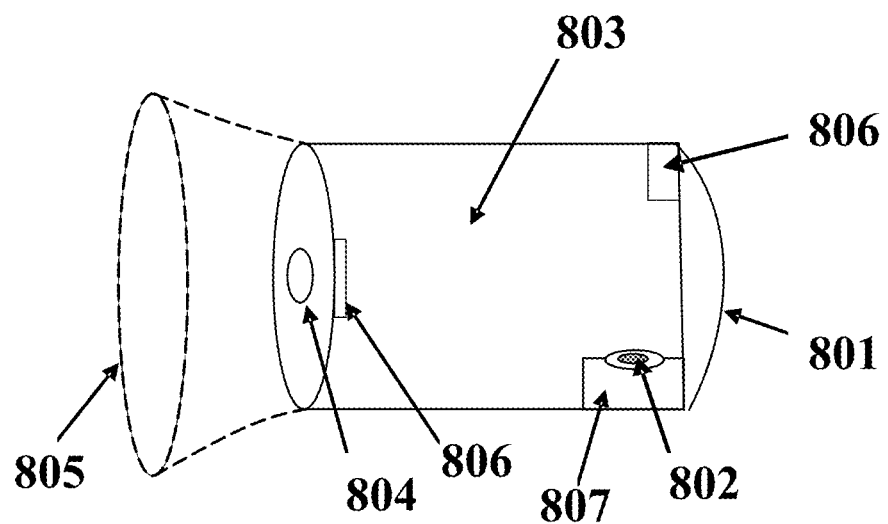
FIG. 8 depicts an exemplary toroidal aerosol delivery system as described herein, wherein the actuator is positioned at the distal end of the aerosol chamber, opposed to the orifice.

In some embodiments, as depicted in FIG. 5, the toroidal aerosol delivery system includes an enclosure (i.e., aerosol chamber 503) from which the toroidal pharmaceutical composition (i.e., toroidal bolus of aerosolized therapeutic agent) is emitted through orifice 504. Aerosol chamber 503 includes at least part of an actuator in mechanical communication with the aerosol chamber, which part of an actuator forms at least part of the enclosure forming the aerosol chamber, depicted for example as element 501 in FIG. 5. In one embodiment, element 501 of FIG. 5 is a flexible membrane forming part of aerosol chamber 503. In some embodiments, the actuator further includes an element in mechanical communication with element 501 to precisely control delivery of aerosolized therapeutic agent. The system further includes an aerosol generator 502, useful for forming the aerosolized therapeutic agent to be administered by the system and useful for charging the system prior to administration of the toroidal pharmaceutical composition. The aerosol generator can include a loaded dose of therapeutic agent 507 to be aerosolized by the action of aerosol generator 502. In some embodiments, the toroidal aerosol delivery system further includes a guide piece 505 external to aerosol chamber 503 (e.g., an eye piece) for controlled, reproducible and/or more comfortable alignment of the system with the target organ (e.g., the eye). In some embodiments, there is provided one or more optional one-way valves (e.g., 506, flap valves as known in the art) for controlled passage of aerosolized therapeutic agent from the system, or for readmission of air after emission of a toroidal bolus (i.e., toroidal pharmaceutical composition) from aerosol chamber 503 through the orifice. In some embodiments, the toroidal pharmaceutical composition resembles a ring torus. In some embodiments, the toroidal pharmaceutical composition resembles a portion of a ring torus. In some embodiments, the orifice is circular. In some embodiments, the orifice is not circular, e.g., square, rectangular, triangular, star-shaped, half-circular, and the like.

In some embodiments, the system includes an element for introducing therapeutic agent to be aerosolized within the aerosol chamber. In some embodiments, as depicted in FIG. 6A, aerosol generator 602 is in communication with loading port 608, through which therapeutic agent is introduced prior to aerosolization. It is understood that the system set forth in FIGS. 6A-6C can additionally include any other element set forth in FIG. 5. Legend of additional depicted elements: orifice (604); aerosol chamber (603); actuator (601).

In some embodiments, the aerosol generator is a vibration mesh ultrasonic nebulizer, as known in the art. In some embodiments, the aerosol generator is a vaporizer. In some embodiments, the aerosol generator is a port from a pressurized system containing therapeutic agent, e.g., a metered valve system as known in the art. In some embodiments, the aerosol generator is a piezoelectric device useful for dispersing therapeutic agent provided in the form of a solid, e.g., a dry powder.

In some embodiments, e.g., as depicted in FIG. 6A, the aerosol generator 602 is in communication with a dose loading chamber 608, which feature is useful for external loading of therapeutic agent prior to aerosolization. In some embodiments, liquid forms of therapeutic agent are provided to the aerosol generator through feature 608. In some embodiments, dry forms of therapeutic agent are provided to the aerosol generator through feature 608.

In some embodiments, e.g., as depicted in FIG. 6B, the aerosol generator 602 is in communication with a dose loading feature 609, both of which are internal to aerosol chamber 603. Legend of additional depicted elements: orifice (604); actuator (601).

In some embodiments, e.g., as depicted in FIG. 6C, the toroidal aerosol delivery system further includes a metering dose button 601 serving the function of the actuator affixed to the body of the aerosol chamber and in fluid communication with it. Legend of additional depicted elements: aerosol chamber (603); orifice (604); loaded dose of therapeutic agent (607); aerosol generator (602); optional guide piece (605).

Further to any embodiment described above, in some embodiments therapeutic agent is provided to the aerosol generator in the form of an encapsulated solution (e.g., blister pack having a fixed volume and load). In some embodiments, therapeutic agent is provided to the aerosol generator in the form of a gel cap. In some embodiments, therapeutic agent is provided to the aerosol generator in the form of a dry powder, which powder is aerosolized by any of a variety of devices known in the art, e.g., piezoelectric device, mesh ultrasonic nebulizer and the like.

In some embodiments, e.g., as depicted in FIG. 7A, the toroidal aerosol delivery system further includes a pressurized cannister 708 containing therapeutic agent, excipients and/or propellant. In some propellant driven embodiments, the chamber is energized by the action of the propellant in response to an actuation (e.g., activating a release valve to allow the chamber to fill under the action of the propellant). Legend of additional depicted elements: actuator (701); aerosol generator (702); aerosol chamber (703); orifice (704); optional guide piece (705).

FIG. 7B depicts another embodiment wherein the volume of the aerosol chamber is reduced relative to that depicted in FIG. 7A. In this embodiment, an internally located aerosol chamber is further depicted. Legend of additional depicted elements: actuator (701); aerosol generator (702); aerosol chamber (703); orifice (704); optional guide piece (705); loaded dose of therapeutic agent (707).

In some embodiments, e.g., as depicted in FIG. 8, the placement of the actuator is at the distal end of the aerosol chamber, opposed to the orifice. Legend of depicted elements; aerosol chamber (803); actuator (801); one-way valve (806); aerosol generator (802); loaded dose of therapeutic agent (807); orifice (804); optional guide piece (805).

In some embodiments, the toroidal aerosol delivery system further incorporates an ocular guide piece (e.g., element 805) for aligning with the eye, as described herein. In some embodiments, the toroidal aerosol delivery system further incorporates a guide suitable for easing administration of a toroidal pharmaceutical composition to another target organ, e.g., ear, throat, nose, bronchus, skin and the like.

In some embodiments, the size of the orifice of the toroidal aerosol delivery system can be conveniently and beneficially varied. In some embodiments, the size of the orifice is determined by an adjustable iris. In some embodiments, the size of the orifice is determined during manufacture by appropriate choice of size. In some embodiments, the orifice can be replaced by any of a variety of sizes. Further to any aspect or embodiment described herein, in some embodiment the orifice size is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 4.0, 5.0 cm, or even larger.

In some embodiments, the toroidal aerosol delivery system further includes a first valve in fluid communication with the orifice, wherein the first valve is adapted for controlled passage of aerosolized therapeutic agent. For example, upon emission of a toroidal pharmaceutical composition in the form of a toroidal bolus and in the absence of the first valve, the aerosol chamber can transiently have an internal pressure less than atmospheric pressure. Accordingly, air would rush into the aerosol chamber to equalize the pressure, and a first valve disposed at the orifice would prevent air from entering the aerosol chamber.

Similarly, in some embodiments, the toroidal aerosol delivery system further includes a second valve in fluid communication with the aerosol chamber. Upon emission of a toroidal pharmaceutical composition, the pressure within the aerosol chamber can be equilibrated with atmospheric pressure by air flow through the second valve.

In some embodiments, the toroidal aerosol delivery system further includes a controller, wherein the controller is adapted to reproducibly provide the necessary force (e.g., mechanical force) to cause emission of the toroidal pharmaceutical composition. In some embodiments, the controller is further adapted to synchronize function of the aerosol generator with actuation resulting in the emission of a toroidal pharmaceutical composition. In some embodiments, the controller includes a lock-out mechanism, which lock-out mechanism can prevent function of the toroidal aerosol delivery system, e.g., repeated administration of toroidal pharmaceutical composition at a rate higher than a prescribed rate.

In another aspect, there is provided a toroidal aerosol delivery system, including a gas reservoir chamber, an in-line aerosol generator adapted to deliver an aerosolized therapeutic agent, an orifice in fluid communication with the gas reservoir chamber and the in-line aerosol generator, the orifice adapted to emit a toroidal pharmaceutical composition, and an actuator in mechanical communication with the gas reservoir chamber.

Figure 9A:
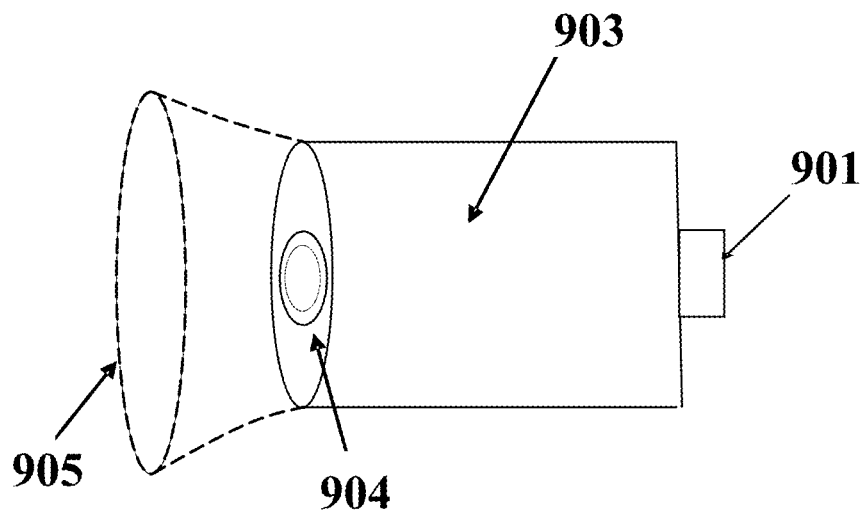
FIG. 9A depicts an exemplary toroidal aerosol delivery system having an in-line aerosol generator as described herein.
Figure 9B:
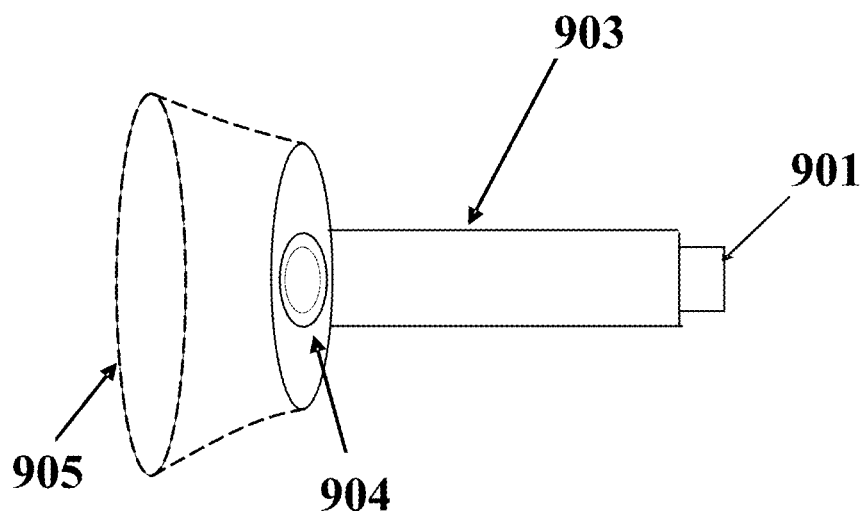
FIG. 9B depicts another embodiment wherein the volume of the gas reservoir is reduced relative to that depicted in FIG. 9A.

In one embodiment, as depicted in FIGS. 9A-9B, the toroidal aerosol delivery system includes an enclosure (i.e., gas reservoir chamber 903) from which a toroidal bolus of gas is emitted through in-line aerosol generator 904. Gas reservoir chamber 903 includes at least part of an actuator in mechanical communication with the gas reservoir chamber, which part of an actuator forms at least part of the enclosure forming the gas reservoir chamber, depicted as element 901 in FIGS. 9A-9B. In one embodiment, element 901 of FIGS. 9A-9B is a flexible membrane forming part of gas reservoir chamber 903. In one embodiment, the actuator further includes an element in mechanical communication with element 901 to precisely control formation of a gas bolus. In one embodiment, the toroidal aerosol delivery system further includes a guide piece 905 external to gas reservoir chamber 903 (e.g., an eye piece) for controlled, reproducible and/or more comfortable alignment of the system with the target organ (e.g., the eye).

In one embodiment, in-line aerosol generator 904 (FIGS. 9A-9B) emits therapeutic agent into the toroidal bolus emitted from gas reservoir chamber 903. In one embodiment, the in-line aerosol generator 904 is an evaporation/condensation devices. In one embodiment, the in-line aerosol generator is a filament coated with therapeutic agent, which therapeutic agent aerosolizes upon heating of the filament. In one embodiment, the in-line aerosol generator includes a plurality of orifices (e.g., jet nozzles) which direct the therapeutic agent into the gas bolus generated from the gas reservoir chamber.

In some embodiments, there is provided one or more optional one-way valves (e.g., flap valves) for controlled passage of aerosolized therapeutic agent from the system, or for readmission of air after emission of a toroidal bolus (i.e., toroidal pharmaceutical composition) from gas reservoir chamber 903 through the orifice. In some embodiments, the toroidal pharmaceutical composition resembles a ring torus. In some embodiments, the toroidal pharmaceutical composition resembles a portion of a ring torus. In some embodiments, the orifice is circular. In some embodiments, the orifice is not circular, e.g., square, rectangular, triangular, star-shaped, half-circular, and the like.

In one embodiment, the volume of the gas reservoir chamber is reduced. See FIGS. 9A and 9B.

In one embodiment, the actuator includes a plurality of actuators, the plurality of actuators including a first actuator in mechanical communication with the gas reservoir chamber and a second actuator in mechanical or electrical communication with the in-line aerosol generator.

In one embodiment, the actutor is further in mechanical or electrical communication with the in-line aerosol generator. In one embodiment, the system is a tunable pulsed toroidal aerosol delivery system. In one embodiment, the toroidal aerosol delivery system further includes an ocular guide piece for aligning with the eye. In one embodiment, the toroidal aerosol delivery system further includes a first valve in fluid communication with the orifice, the first valve adapted for controlled passage of aerosolized therapeutic agent. In one embodiment, the toroidal aerosol delivery system further includes a second valve in fluid communication with the gas reservoir chamber, the second valve adapted for controlled passage of air. In one embodiment, the actuator includes a controller, wherein the controller is adapted to reproducibly provide a mechanical force. In one embodiment, the controller is further adapted to synchronize the in-line aerosol generator function with the actuator function. In some embodiments, the controller includes a lock-out mechanism, which lock-out mechanism can prevent function of the toroidal aerosol delivery system, e.g., repeated administration of toroidal pharmaceutical composition at a rate higher than a prescribed rate.

Without wishing to be bound by any theory, it is believed that a number of factors must be considered in the design and use of the methods and devices described herein. Specifically, these factors include the placement of the aerosol generator within the aerosol chamber. It is believed that placement of the aerosol generator toward the back of the aerosol chamber, i.e., distal from the orifice, successfully results in aerosolization. However, placement of the aerosol generator less distal from the orifice can result in more homogeneous distribution of particles. Moreover, the length and girth of the aerosol chamber can be modulated to produce toroidal pharmaceutical compositions which are optimized for a particular target organ, e.g., the eye. Moreover, the degree of energizing of the aerosol chamber is a parameter to be optimized. For example, as described herein, the force applied as a function of time to the actuator can be optimized for toroidal size, toroidal volume, and directional velocity of the resulting toroidal pharmaceutical composition.

V. Additional Embodiments

In another aspect, there is provided a toroidal pharmaceutical composition including an ophthalmically active pharmaceutical ingredient. In one embodiment, the toroidal pharmaceutical composition is dispensed from a toroidal aerosol delivery system. In one embodiment, the toroidal aerosol delivery system includes an aerosol chamber, an aerosol generator in fluid communication with the aerosol chamber, in which the aerosol generator is adapted to charge the aerosol chamber with an aerosolized ophthalmically active pharmaceutical ingredient, an orifice in fluid communication with the aerosol chamber, the orifice adapted to emit said toroidal pharmaceutical composition; and an actuator in mechanical communication with said aerosol chamber. In one embodiment, the toroidal aerosol delivery system includes a gas reservoir chamber, an in-line generator adapted to deliver an aerosolized ophthalmically active pharmaceutical ingredient, an orifice in fluid communication with the gas reservoir chamber and the in-line aerosol generator, the orifice adapted to emit the toroidal pharmaceutical composition; and an actuator in mechanical communication with the gas reservoir chamber.

It is understood that the methods and devices described herein can be employed in a variety of uses. In one embodiment, an agent (e.g., a therapeutic agent) is beneficially transmitted at a distance from a target organ of a subject. Administration at a distance is useful, for example, to avoid contamination of the administrating device, e.g., an orifice or therapeutic agent reservoir. Cases in which contamination is preferentially avoided include the treatment of infection disease or the administration of vaccine. Additionally, administration at a distance is beneficial, for example, in allowing for multiple dose applications without contamination of the device or therapeutic agent reservoir. Moreover, because particle density can be controlled during the generation of the pharmaceutical composition, the therapeutic agent can be stored in a reservoir at higher concentrations than available for other methods of administration, e.g., aerosolized plume methods. Moreover, higher therapeutic agent concentration in a reservoir can be self-preserving due to inhibition of microbial growth, due e.g., to osmotic effects of higher therapeutic agent concentration.

In one embodiment, veterinary administration of a therapeutic agent is conducted at a distance, e.g., 1, 2, 3, 4, 5, 10, 15, 20, 25, 30, 40, 50 and even 60 feet removed from the subject (e.g., domestic animal or wildlife).

In one embodiment, administration for self-defense is conducted, wherein the administered agent is a noxious agent designed to deter the actions (e.g., threatening behavior) of a subject (e.g., human or wildlife).

VI. Examples

Example 1

Determination of Geometric Parameters

The width and height of toroidal boli resulting from methods and devices described herein can be investigated by a variety of methods, including high-speed (e.g., stroboscopic) photographic analysis. As shown in FIG. 10A, width can be calculated by visual inspection of a sufficiently high-speed photograph of the torus. In FIG. 10A, the width of the torus is approximately 1-in, which corresponds to the vertical extent of the torus. Similarly, the height of the torus, corresponding to the widest extent of the torus as viewed along the axis of propagation (i.e., axis of revolution described herein), can be determined by inspection. As shown in FIG. 10B, the overall height of the torus is about 1.8-cm, and the ring portion is about 0.4-cm. Thus, the internal void of the torus as viewed along the axis of propagation is about 1.0 cm.

Example 2

Determining Directional Movement of Tori

Determination of the direction movement, e.g., velocity, dispersion, and the like, of a torus described herein can be achieved by a variety of methods known in the art, including stroboscopic photography. For example, as depicted in FIG. 11, a torus was emitted from a device described herein and followed in time with stroboscopic flashes of known timing and duration. Accordingly, the torus can be observed at known times and distances, allowing the calculation of the speed of propagation.

Example 3

Refined Measurement of Torus Size Parameters

Figure 12:
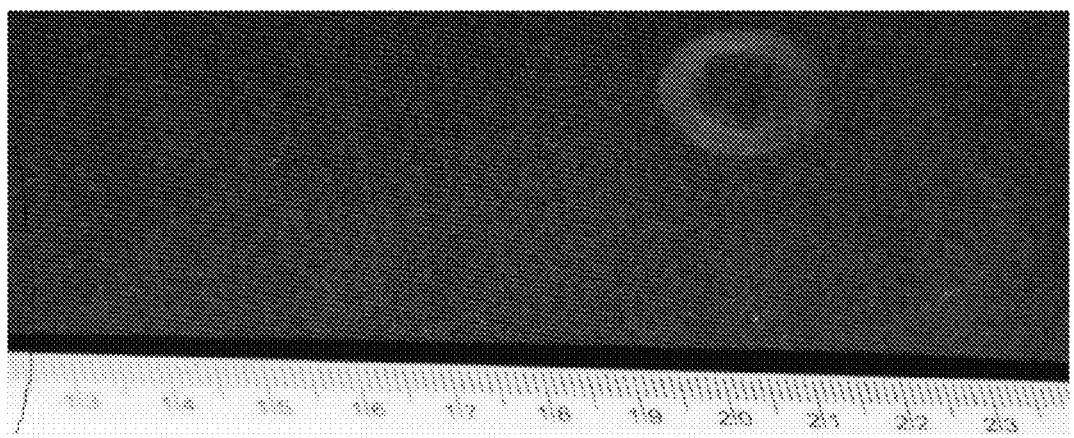
FIG. 12 depicts the result of impinging a toroidal pharmaceutical composition as described herein on a semi-translucent cloth surface, as viewed along the direction of propagation.

A variety of methods are available to accurately and precisely determine the overall height of a torus as described herein. For example, FIG. 12 depicts the result of impinging a torus as described herein on a semi-translucent cloth surface. As depicted in FIG. 12, the height of the torus is about 1.8 cm. See also Example 1.

Example 4

Determination of Toroidal Volume

Figure 13:
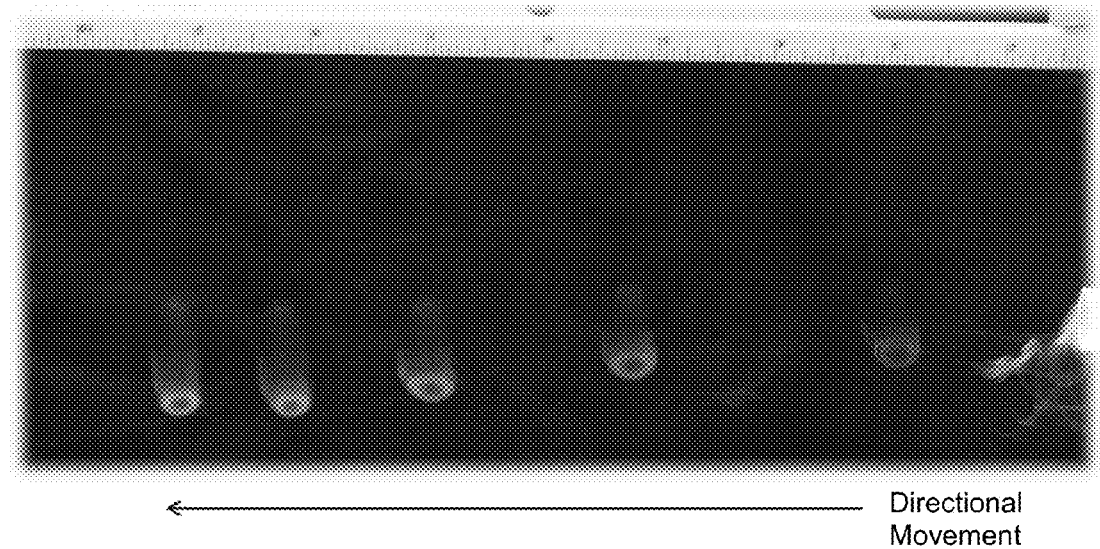
FIG. 13 depicts a toroidal pharmaceutical composition in time via stroboscopic photography.

Determination of toroidal volume of a torus emitted by a device described herein can be conducted by a variety of methods known in the art. For example, as depicted in FIG. 13, a torus including a toroidal bolus of an aerosolized agent (e.g., theatrical smoke in the current example) was emitted at the orifice of a device described herein, shown in FIG. 13 at the right edge. The torus was observed by stroboscopic photography as it propagated from right to left with time. Analysis of the resulting torus according to Eqn. 1 provided a major toroidal radius of 1.25-cm, a ring toroidal radius of 0.5-cm, and a resulting volume of 6.19 $cm^3$. Additionally, FIG. 13 depicts that while the major toroidal radius and ring toroidal radius may change with time during propagation, the resulting volume of the torus can remain constant, as would be expected by the conservation of mass of the toroidal bolus assuming a constant density of aerosolized agent and insubstantial dispersal.

Figure 14:
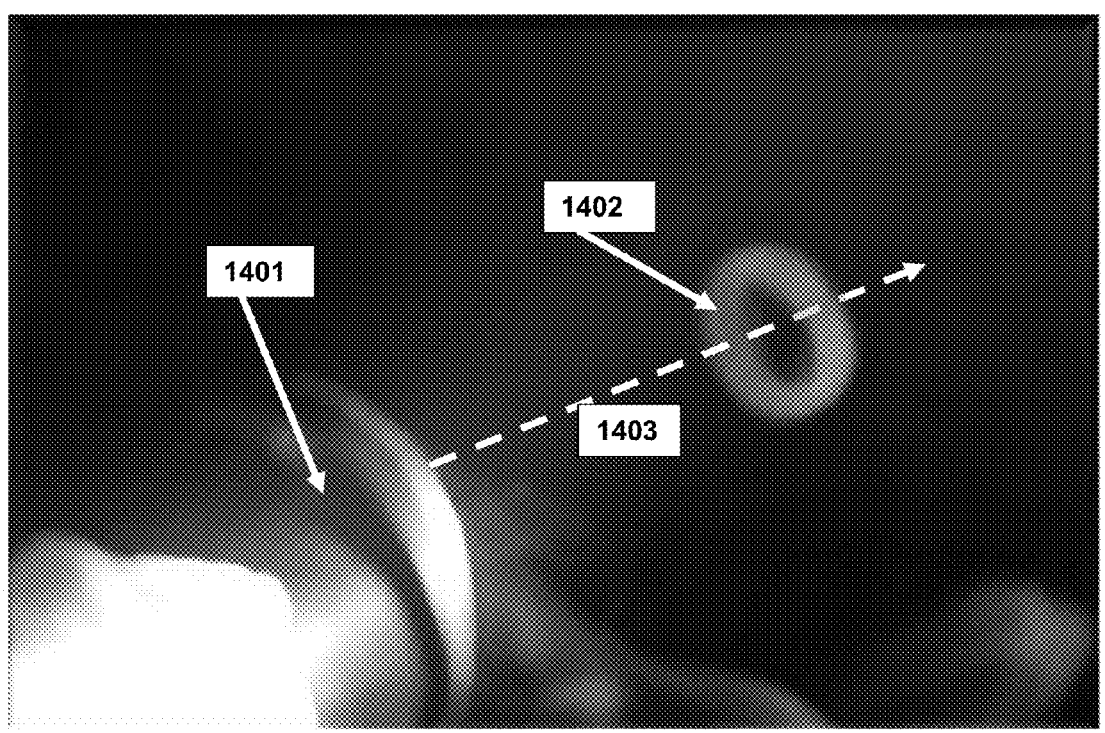
FIG. 14 depicts a toroidal pharmaceutical composition 1402 emitted from orifice 1401, and photographically captured as it propagated along the axis of propagation 1403.

A further exemplary toroidal bolus is depicted in FIG. 14. In the figure, a toroidal bolus 1402 has been emitted from orifice 1401, and photographically captured as it propagated along the axis of propagation 1403.

Example 5

Impingement on Target Organs

Figure 15A:
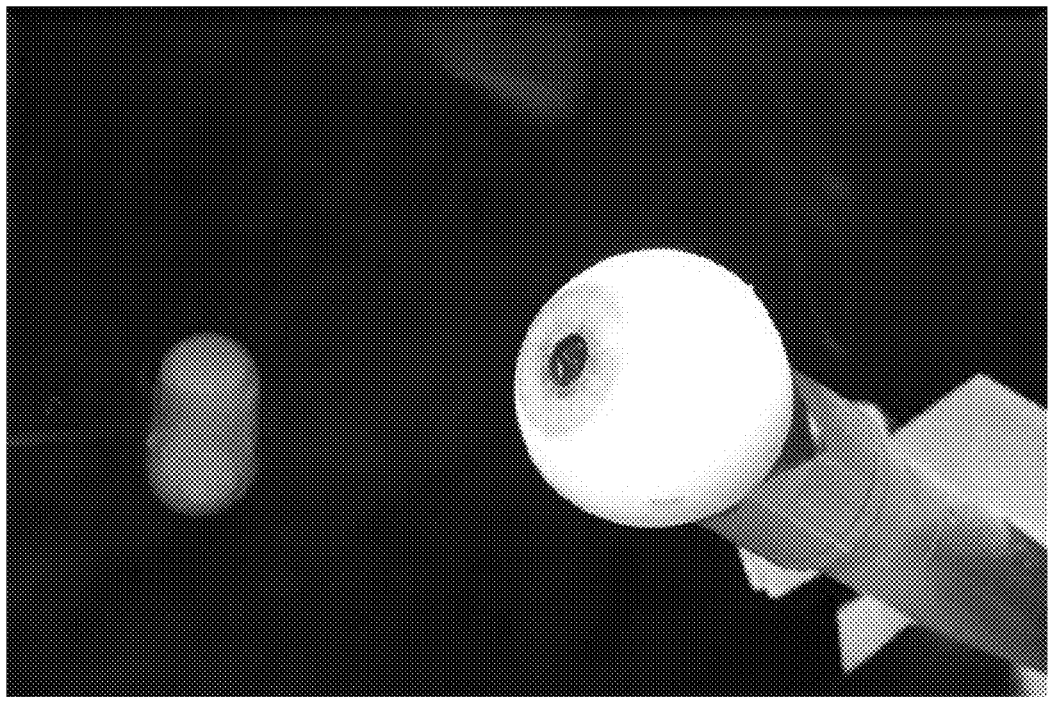
FIG. 15A depicts a toroidal pharmaceutical composition as observed during propagation toward an exemplary target organ, i.e., an artificial eye.
Figure 15B:
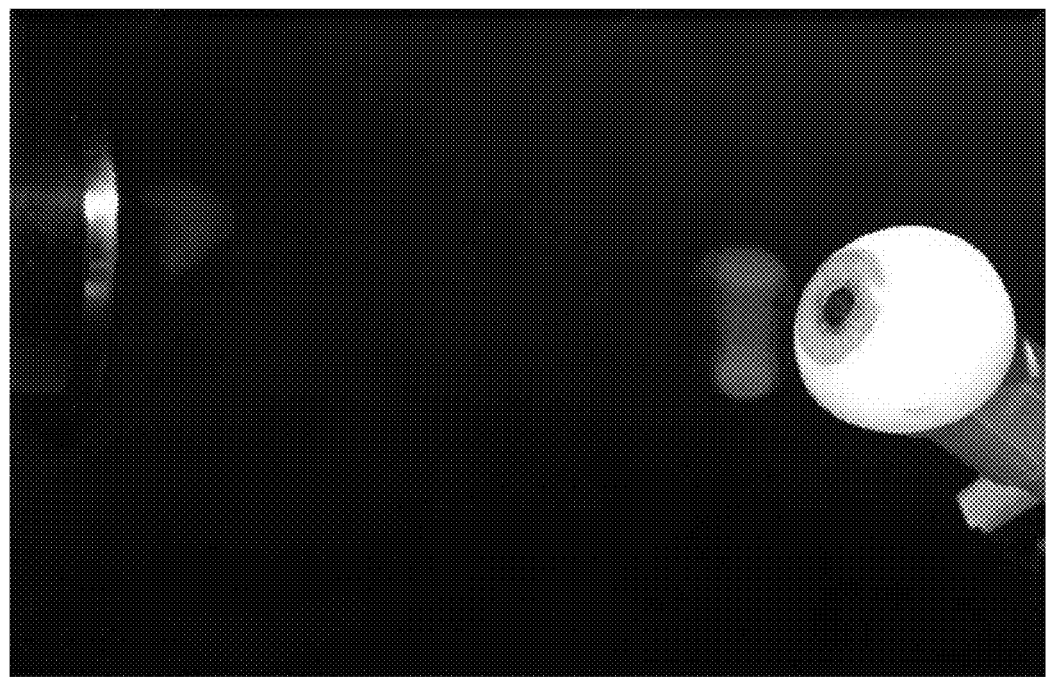
FIG. 15B depicts the toroidal pharmaceutical composition about to impact the target organ.
Figure 15C:
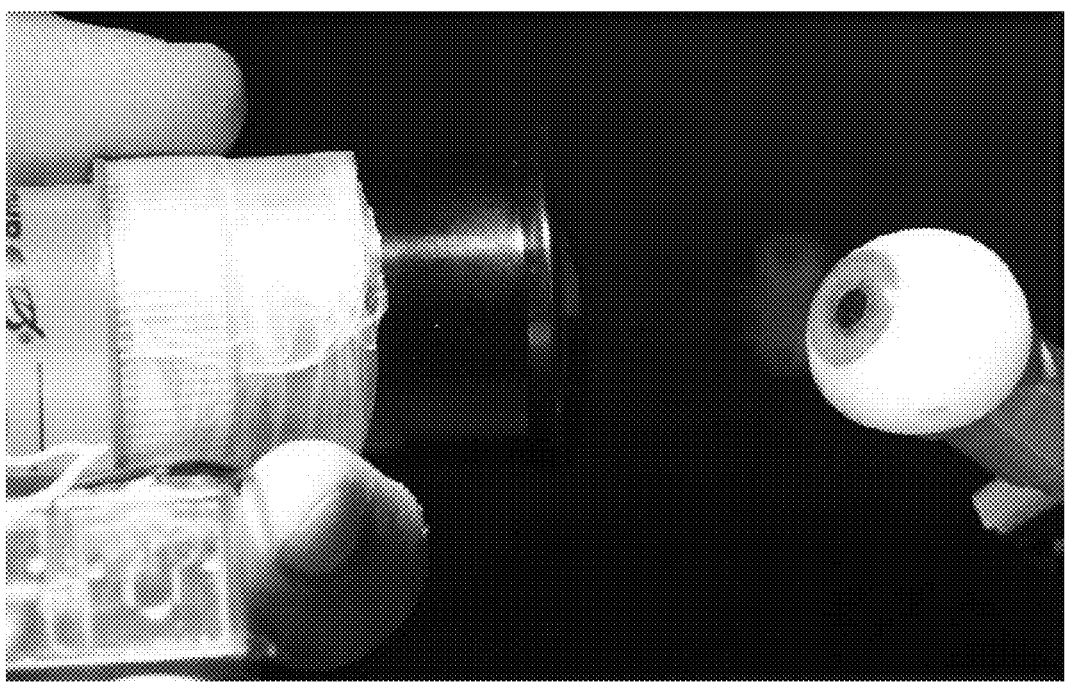
FIG. 15C depicts that the orifice emitting the toroidal pharmaceutical composition can be close to the target organ.

The toroidal bolus of aerosolized therapeutic agent can be directed at a target organ. As depicted in FIG. 15A, a toroidal bolus of appropriate size is observed in propagation toward an exemplary target organ surrogate, i.e., an artificial eye. FIG. 15B depicts the toroidal bolus about to impact the target organ. As depicted in FIG. 15C, the orifice emitting the toroidal bolus can be quite close to the target organ.

Example 6

Toxoid Deposition Sample Analysis

A variety of methods are available to quantify the amount of aerosolized agent deposited on a target organ by the methods and devices described herein.

In one experiment, an aerosolized agent entrained within the toroidal bolus included a fluorescent agent (i.e., fluorescein) which could be assayed in order to determine the degree of deposition. Multiple administrations of toroidal boli were conducted, and the results were averaged. The source was a device as described herein which provides a toroidal bolus. The target was a crystalline surface which was quantitatively washed and assayed (i.e., fluorescence determination) for deposition of fluorescein. As shown in Table 1 following, deposition of aerosolized agent can be determined by analytical methods known in the art.

TABLE 1

| # Toroids | Sample conc., wt-% | Dil. Vol, mL | Dil. factor | Fluor units | Conc. ng/mL | Deposition, ng | Dose, ng/toroid |
|---|---|---|---|---|---|---|---|
| 10 | 0.25% | 1 | 2 | 41397 | 125.27 | 125.3 | 12.5 |
| 10 | 0.05% | 1 | 2 | 10000 | 29.56 | 29.6 | 3.0 |

Figure 16A:
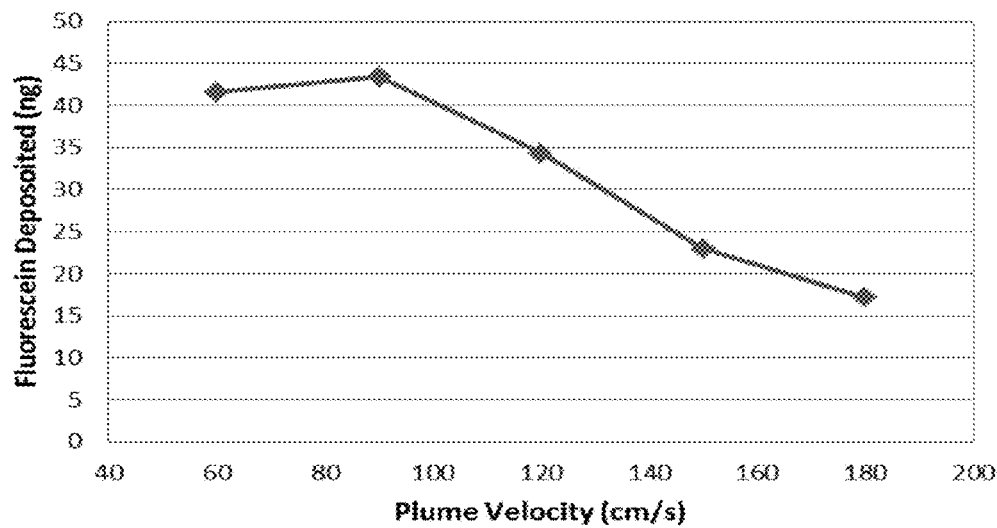
FIG. 16A depicts the dependence of the amount of deposition on plume velocity (cm/s) for a 0.05% fluorescein solution formulated into a toroidal bolus which was impinged on a target with analogous surface geometry to that of a human eye. Ordinate: fluorescein deposition (ng). See Example 6.

In another experiment to determine the deposition on a target of compounds entrained within a toroidal bolus, a 0.05% fluorescein solution was aerosolized into an aerosol chamber, and the device was actuated at different forces to form and propagate drug loaded toroidal boli at varying velocities. These velocities were documented/measured using videographic methods known in the art. These toroids where then impacted on a surface with analogous surface geometry to that of a human eye, i.e., a prosthetic ocular device. After the toroidal impaction onto the surface, the active substance (i.e., fluoroscein) was extracated with a suitable solvent and the fluoroscein content was quantified by fluorescence spectroscopy. As shown in FIG. 16A, emission velocity was plotted versus deposition to characterize the deposition of fluoroescein. Without wishing to be bound by any theory, it is observed that higher plume velocity results in lower deposition of fluoroscein under these conditions.

Figure 16B:
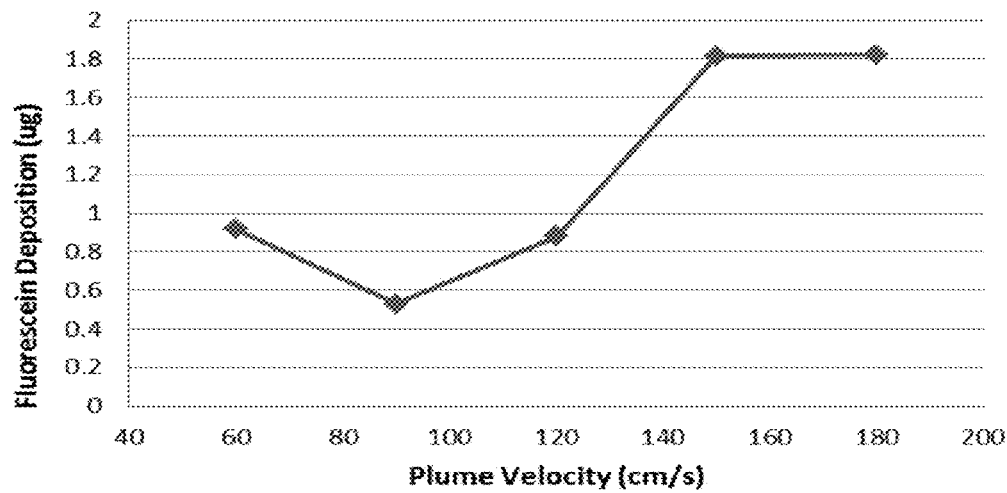
FIG. 16B depicts the results of deposition on plume velocity for a 5% fluorescein solution. Ordinate: fluorescein depoisition (μg).

FIG. 16B depicts an analogous experiment employing 5% fluoroescein solution. Without wishing to be bound by any theory, it is observed that higher plume velocity results in higher deposition of fluoroescein under these conditions.

Example 7

Aerosol Particle Sizing

Aerosol particle sizing employing, e.g., laser diffraction methodology, is useful in characterizing the density and/or particle size distribution of particles forming the toroidal pharmaceutical composition disclosed herein.

In a first experiment to determine the geometric particle size and optical density of drug loaded tori, a Sympatec-HELOS instrument equipped with an inhalation aerosol testing apparatus was utilized, as known in the art. To prepare samples, a solution of fluorescein Na was formulated in normal saline solution (0.9% NaCl). This solution was loaded to the Aerosol generator (AG) of the device. The AG was turned on, aerosol was allowed to fill the Aerosol chamber. Once the chamber was filled, the AG was turned off. The dosing button of the toroidal aerosol delivery system was actuated and toroidal pulses of aerosol were emitted through the laser beam of the Sympatec device with the data acquisition software turned on. The Sympatec-HELOS software then calculated and determined the ×10, ×50, ×90 (particle size distribution as known in the art), density distribution and cumulative distribution.

Figure 17A:
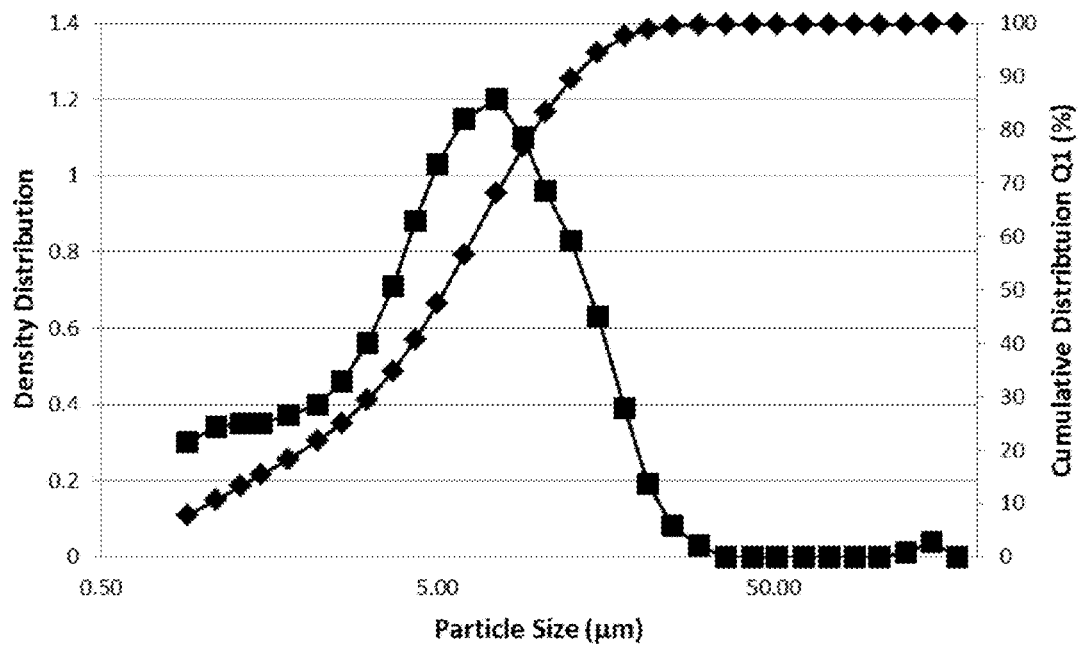
FIG. 17A employed 0.05% fluorescein solution.

FIG. 17A provides the result of 0.05% fluorescein, depicting density distribution (left axis) and concentration distribution (right axis) against particle size (log axis). For these data, ×10=1.06 µm, ×50=5.28 µm, and ×90=12.73 µm.

Figure 17B:
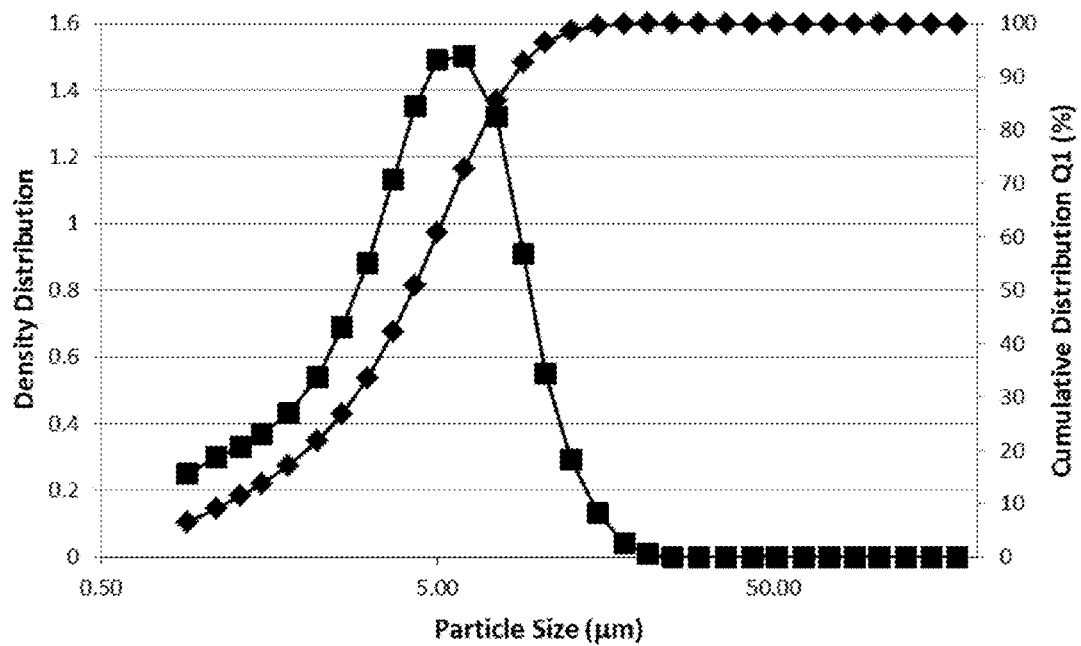
FIG. 17B employed 5.0% fluorescein solution. Axes (FIGS. 17A-17B): x-axis: particle size (μm) (log scale display); left y-axis (boxes): density distribution; right y-axis (diamonds): cumulative distribution Q1 (%).

FIG. 17B provides the result of 5.0% fluorescein, depicting density distribution (left axis) and concentration distribution (right axis) against particle size (log axis). For these data, ×10=1.18 µm, ×50=4.23 µm, and ×90=8.44 µm.

Figure 18A:
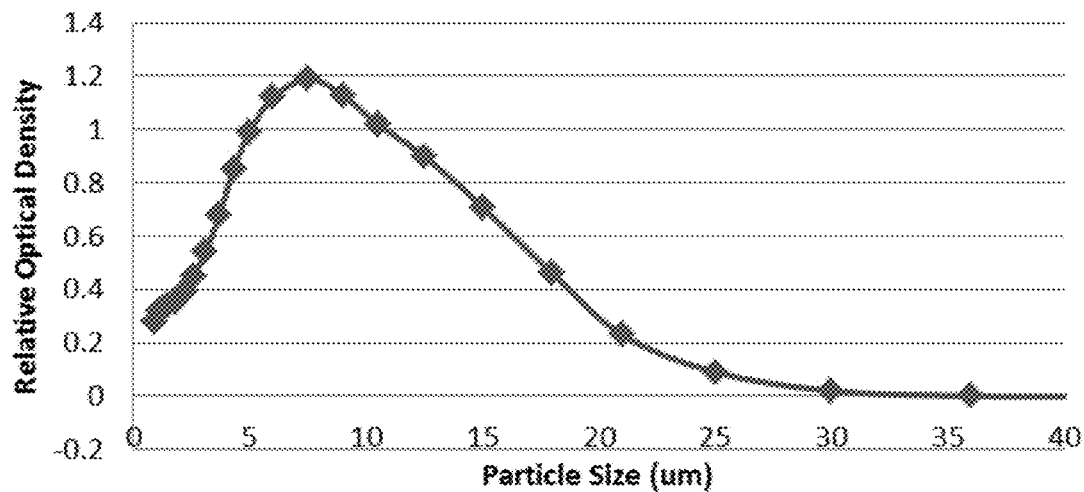
FIGS. 18A-18B depict relative optical density (y-axis) against particle size for experiments conducted with the Sympatec-HELOS device. See Example 7.
Figure 18B:
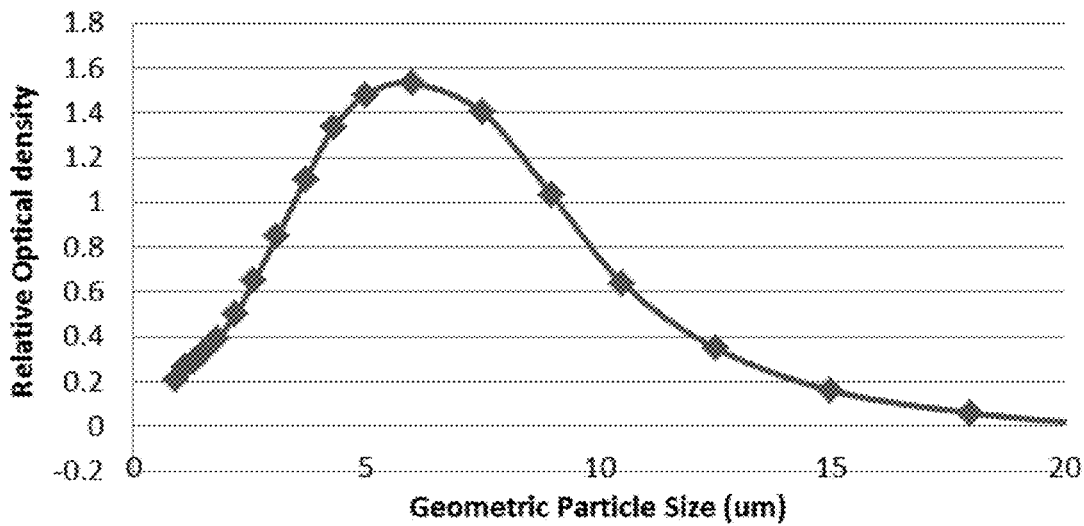

In another experiment, the Sympatec-HELOS system was employed with a toroidal aerosol delivery system to further investigate the toroidal boli. FIG. 18A depicts the relative optical density of 0.05% fluorescein solution toroidal boli as a function of particle size (geometric size). For this set of observations, ×10=1.12 µm, ×50=5.55 µm, and ×90=13.37 µm. FIG. 18B depicts the relative optical density of 5.0% fluorescein solution toroidal boli as a function of particle size. For this set of observations, ×10=1.31 µm, ×50=4.46 µm, and ×90=8.76 µm.

Example 8

Dose Content Analysis

Dose content uniformity of toroidal pharmaceutical compositions as described herein was determined by methods well known in the pharmaceutical arts. A series of sample toroidal pharmaceutical compositions using fluorescein (0.05%) as a surrogate for a pharmaceutical agent were emitted into a dose content uniformity apparatus. As known in the art, the dose content uniformity apparatus provides a directing tube with a distal filter and vacuum system designed to capture the contents emitted into the tube on the filter. The number of emissions was 10. The dilution volume was 10 mL. The dilution factor was 2. In one experiment, the number of fluorescent units was 52,622, corresponding to a total concentration of 1595.49 ng/mL fluorescein. The total mass in 10 toroidal pharmaceutical composition emissions was 1594.9 ng, and the mass per single toroidal pharmaceutical composition was 159.5 ng.

Example 9

Toroidal Drug Loading Assay

Figure 19:
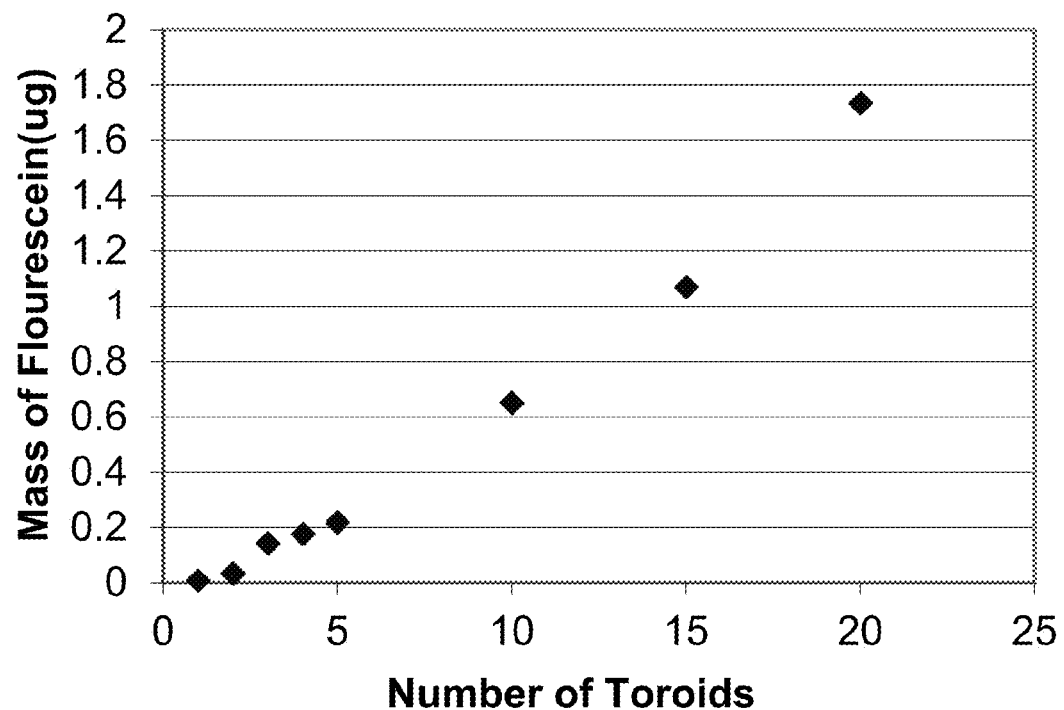
FIG. 19 depicts the dependence of the amount of fluorescein captured in a vacuum assay system as a function of the number of toroidal boli ("Number of Toroids") impinged on the target. See Example 9.

To determine the amount of active substance (e.g., fluorescein) emitted from the toroidal aerosol delivery system in each bolus, a sample collection tube was affixed with an appropriate filter for retaining aerosol under vacuum. A dosed known numbers of toroidal boli were emitted into the sample filter for extraction and assay. The amount of fluorescein contained in each unit was found to be very reproducible and to increase proportionally to how many units were dosed. For this formulation the mass loading for each torroid was found to be about 43.75 ng for 0.05% solution and 2.13 ug for the 5% solution. As depicted in FIG. 19 the mass of fluorescein detected increases monotonically with the number of toroidal boli captured.

Example 10

Liquid Aerosolization Rate Studies

Figure 20:
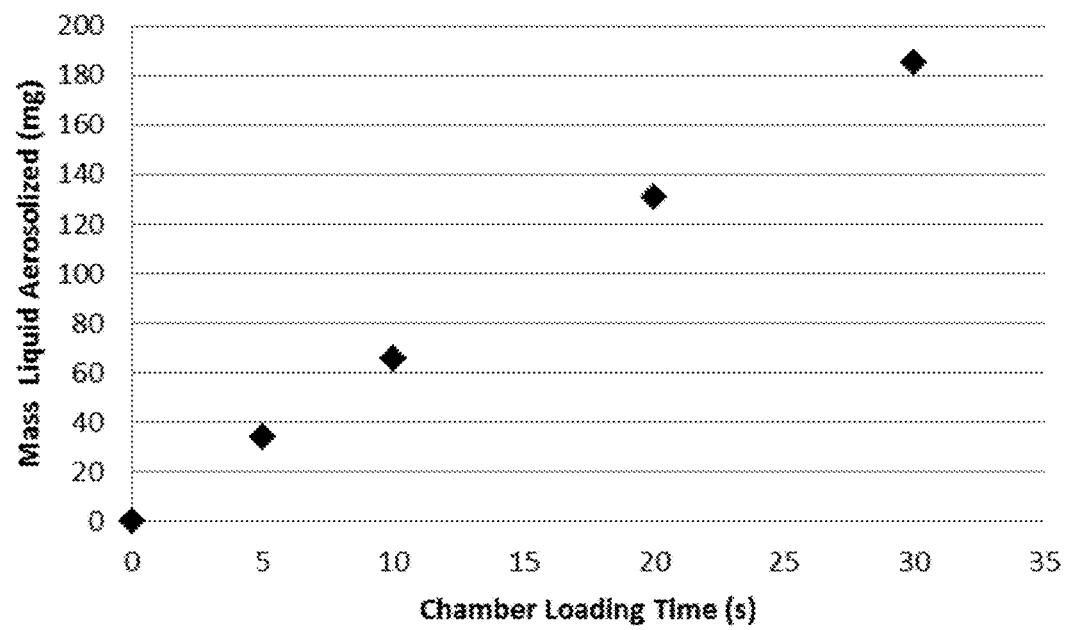
FIG. 20 depicts the dependence of the mass amount of liquid aerosolized (mg) as a function of the time for chamber loading (sec).

The extent and rate of liquid aerosolization was investigated as a function of chamber loading time for the toroidal aerosol delivery system described above. As shown in FIG. 20, the mass amount of liquid aerosolized is an approximately linear function of the time for chamber loading.

VII. Embodiments

Embodiment 1

A method for administering a toroidal pharmaceutical composition to a subject, said method comprising: dispensing a toroidal pharmaceutical composition from a toroidal aerosol delivery system, said toroidal pharmaceutical composition comprising an aerosolized therapeutic agent; and allowing said toroidal pharmaceutical composition to contact a target organ of said subject, thereby administering said toroidal pharmaceutical composition.

Embodiment 2

The method of embodiment 1, wherein said dispensing comprises: charging a toroidal aerosol delivery system, thereby providing a charged toroidal aerosol delivery system; and actuating said charged toroidal aerosol delivery system.

Embodiment 3

The method of one of embodiments 1 or 2, wherein said toroidal aerosol delivery system comprises: an aerosol chamber; an aerosol generator in fluid communication with said aerosol chamber, said aerosol generator adapted to charge said aerosol chamber with said aerosolized therapeutic agent; an orifice in fluid communication with said aerosol chamber, said orifice adapted to emit said toroidal pharmaceutical composition; and an actuator in mechanical communication with said aerosol chamber.

Embodiment 4

The method of embodiment 3, wherein said charging comprises delivering a non-aerosolized therapeutic agent into said aerosol generator; and allowing said aerosol generator to produce said aerosolized therapeutic agent from said non-aerosolized therapeutic agent and delivering said aerosolized therapeutic agent to said aerosol chamber, thereby charging said charged toroidal aerosol delivery system.

Embodiment 5

The method of embodiment 3, wherein said actuating comprises energizing said actuator.

Embodiment 6

The method of embodiment 5, wherein said energizing comprises applying a mechanical force to said actuator.

Embodiment 7

The method of embodiment 5, wherein the pressure within said aerosol chamber increases as a result of said energizing.

Embodiment 8

The method of any one of embodiments 1 to 7, wherein said toroidal pharmaceutical composition is substantially intact upon contacting said target organ.

Embodiment 9

The method of any one of embodiments 1 to 8, wherein said target organ is the eye, ear, nose, or throat.

Embodiment 10

The method of embodiment 9, wherein said target organ is an eye.

Embodiment 11

The method of embodiment 9, said subject is a mammalian subject.

Embodiment 12

The method of embodiment 11, wherein said subject is a human subject.

Embodiment 13

The method of one of embodiments 1 or 2, wherein said toroidal aerosol delivery system comprises: a gas reservoir chamber; an in-line aerosol generator adapted to deliver said aerosolized therapeutic agent; an orifice in fluid communication with said gas reservoir chamber and said in-line aerosol generator, said orifice adapted to emit said toroidal pharmaceutical composition; and an actuator in mechanical communication with said gas reservoir chamber.

Embodiment 14

The method of embodiment 13, wherein said actuator comprises a plurality of actuators, said plurality of actuators comprising a first actuator in mechanical communication with said gas reservoir chamber and a second actuator in mechanical or electrical communication with said in-line aerosol generator.

Embodiment 15

The method of embodiment 13, wherein said actuator is further in mechanical or electrical communication with said in-line aerosol generator.

Embodiment 16

The method of embodiment 13, wherein said actuating comprises energizing said actuator.

Embodiment 17

The method of embodiment 16, wherein said energizing comprises applying a mechanical force to said actuator.

Embodiment 18

The method of embodiment 16, wherein the pressure within said aerosol chamber increases as a result of said energizing.

Embodiment 19

The method of embodiment 14, wherein said actuating comprises energizing said first actuator and said second actuator.

Embodiment 20

The method of any one of embodiments 13 to 19, wherein said toroidal pharmaceutical composition is substantially intact upon contacting said target organ.

Embodiment 21

The method of any one of embodiments 13 to 20, wherein said target organ is the eye, ear, nose, or throat.

Embodiment 22

The method of embodiment 21, wherein said target organ is an eye.

Embodiment 23

The method of embodiment 21, said subject is a mammalian subject.

Embodiment 24

The method of embodiment 23, wherein said subject is a human subject.

Embodiment 25

A toroidal aerosol delivery system, comprising: an aerosol chamber; an aerosol generator in fluid communication with said aerosol chamber; an orifice in fluid communication with said aerosol chamber; and an actuator in mechanical communication with said aerosol chamber.

Embodiment 26

The toroidal aerosol delivery system of embodiment 25, wherein said system is a tunable pulsed toroidal aerosol delivery system.

Embodiment 27

The toroidal aerosol delivery system of any one of embodiments 25 to 26, wherein said aerosol generator is adapted to charge said aerosol chamber with an aerosolized therapeutic agent.

Embodiment 28

The toroidal aerosol delivery system of any of embodiments 25 to 27, further comprising an ocular guide piece for aligning with the eye.

Embodiment 29

The toroidal aerosol delivery system of any of embodiments 25 to 28, further comprising a first valve in fluid communication with said orifice, said first valve adapted for controlled passage of aerosolized therapeutic agent.

Embodiment 30

The toroidal aerosol delivery system of any of embodiments 25 to 29, further comprising a second valve in fluid communication with said aerosol chamber, said second valve adapted for controlled passage of air.

Embodiment 31

The toroidal aerosol delivery system of any of embodiments 25 to 30, wherein said actuator comprises a controller, wherein said controller is adapted to reproducibly provide a mechanical force.

Embodiment 32

The toroidal aerosol delivery system of embodiment 31, wherein said controller is further adapted to synchronize said aerosol generator function with the function of said actuator.

Embodiment 33

The toroidal aerosol delivery system of embodiment 31, wherein said controller comprises a lock-out mechanism.

Embodiment 34

A toroidal aerosol delivery system, comprising: a gas reservoir chamber; an in-line aerosol generator adapted to deliver an aerosolized therapeutic agent; an orifice in fluid communication with said gas reservoir chamber and said in-line aerosol generator, said orifice adapted to emit a toroidal pharmaceutical composition; and an actuator in mechanical communication with said gas reservoir chamber.

Embodiment 35

The toroidal aerosol delivery system of embodiment 34, wherein said actuator comprises a plurality of actuators, said plurality of actuators comprising a first actuator in mechanical communication with said gas reservoir chamber and a second actuator in mechanical or electrical communication with said in-line aerosol generator.

Embodiment 36

The toroidal aerosol delivery system of embodiment 34, wherein said actuator is further in mechanical or electrical communication with said in-line aerosol generator.

Embodiment 37

The toroidal aerosol delivery system of one of embodiments 34 to 36, wherein said system is a tunable pulsed toroidal aerosol delivery system.

Embodiment 38

The toroidal aerosol delivery system of any one of embodiments 34 to 37, further comprising an ocular guide piece for aligning with the eye.

Embodiment 39

The toroidal aerosol delivery system of any one of embodiments 34 to 38, further comprising a first valve in fluid communication with said orifice, said first valve adapted for controlled passage of aerosolized therapeutic agent.

Embodiment 40

The toroidal aerosol delivery system of any one of embodiments 34 to 39, further comprising a second valve in fluid communication with said gas reservoir chamber, said second valve adapted for controlled passage of air.

Embodiment 41

The toroidal aerosol delivery system of any of embodiments 34 to 40, wherein said actuator comprises a controller, wherein said controller is adapted to reproducibly provide a mechanical force.

Embodiment 42

The toroidal aerosol delivery system of embodiment 41, wherein said controller is further adapted to synchronize said in-line aerosol generator function with said actuator function.

Embodiment 43

A method for administering an aerosolized ophthalmically active pharmaceutical ingredient to a subject in need thereof, said method comprising administering an effective amount of a toroidal pharmaceutical composition to an eye of said subject, wherein said toroidal pharmaceutical composition comprises said aerosolized ophthalmically active pharmaceutical ingredient.

Embodiment 44

The method of embodiment 43, wherein said subject is a mammalian subject.

Embodiment 45

The method of embodiment 44, wherein said subject is a human subject.

Embodiment 46

The method of one of embodiments 43 to 45, wherein said administering comprises: charging a toroidal aerosol delivery system, thereby providing a charged toroidal aerosol delivery system; and actuating said toroidal aerosol delivery system.

Embodiment 47

The method of embodiment 46, wherein said toroidal aerosol delivery system comprises: an aerosol chamber; an aerosol generator in fluid communication with said aerosol chamber, said aerosol generator adapted to charge said aerosol chamber with said aerosolized ophthalmically active pharmaceutical ingredient; an orifice in fluid communication with said aerosol chamber, said orifice adapted to emit said toroidal pharmaceutical composition; and an actuator in mechanical communication with said aerosol chamber.

Embodiment 48

The method of embodiment 46, wherein said toroidal aerosol delivery system comprises: a gas reservoir chamber; an in-line aerosol generator adapted to deliver said aerosolized ophthalmically active pharmaceutical ingredient; an orifice in fluid communication with said gas reservoir chamber and said in-line aerosol generator, said orifice adapted to emit said toroidal pharmaceutical composition; and an actuator in mechanical communication with said gas reservoir chamber.

Embodiment 49

A toroidal pharmaceutical composition comprising an ophthalmically active pharmaceutical ingredient.

What is claimed is:

1. A method for administering a toroidal pharmaceutical composition to a subject, said method comprising:
   dispensing a toroidal pharmaceutical composition from a toroidal aerosol delivery system thereby forming a dispensed toroidal pharmaceutical composition, said dispensed toroidal pharmaceutical composition comprising an aerosolized therapeutic agent within a toroidal vortex with a directional velocity and an internal rotational velocity; and
   allowing said dispensed toroidal pharmaceutical composition to contact a target organ of said subject, thereby administering said toroidal pharmaceutical composition, which maintains its size and shape along an uncontained axis of propagation.

2. The method of claim 1, wherein said dispensing comprises:
   charging a toroidal aerosol delivery system, thereby providing a charged toroidal aerosol delivery system; and
   actuating said charged toroidal aerosol delivery system, wherein said actuating provides a force resulting in a toroidal rotational velocity sufficiently high to allow said toroidal pharmaceutical composition to remain substantially intact until contacting said target organ.

3. The method of claim 1, wherein said toroidal aerosol delivery system comprises:
   an aerosol chamber;
   an aerosol generator in fluid communication with said aerosol chamber, said aerosol generator adapted to charge said aerosol chamber with said aerosolized therapeutic agent;
   an orifice in fluid communication with said aerosol chamber, said orifice adapted to emit said toroidal pharmaceutical composition; and
   an actuator in mechanical communication with said aerosol chamber adapted to transiently increase pressure within said aerosol chamber sufficient to emit said toroidal pharmaceutical composition through the orifice.

4. The method of claim 1, wherein said toroidal aerosol delivery system comprises:
   a gas reservoir chamber;
   an in-line aerosol generator adapted to deliver said aerosolized therapeutic agent;
   an orifice in fluid communication with said gas reservoir chamber and said in-line aerosol generator, said orifice adapted to emit said toroidal pharmaceutical composition; and
   an actuator in mechanical communication with said gas reservoir chamber adapted to transiently increase pressure within said aerosol chamber sufficient to emit said toroidal pharmaceutical composition through the orifice.

5. The method of claim 4, wherein said actuator comprises a plurality of actuators, said plurality of actuators comprising a first actuator in mechanical communication with said gas reservoir chamber and a second actuator in mechanical or electrical communication with said in-line aerosol generator.

6. A toroidal aerosol delivery system, comprising:
   an aerosol chamber;
   an aerosol generator in fluid communication with said aerosol chamber;
   an orifice in fluid communication with said aerosol chamber; and
   an actuator in mechanical communication with said aerosol chamber adapted to transiently increase pressure within said aerosol chamber sufficient to emit a toroidal pharmaceutical composition comprising an aerosolized therapeutic agent within a toroidal vortex through the orifice, said toroidal vortex having a directional velocity and an internal rotational velocity, wherein the composition maintains its size and shape along an uncontained axis of propagation.

7. The toroidal aerosol delivery system of claim 6, further comprising a first valve in fluid communication with said orifice, said first valve adapted for controlled passage of aerosolized therapeutic agent.

8. The toroidal aerosol delivery system of claim 6, further comprising a second valve in fluid communication with said aerosol chamber, said second valve adapted for controlled passage of air.

9. The toroidal aerosol delivery system of claim 6, wherein said actuator is adapted to provide a force resulting in a toroidal rotational velocity sufficiently high to allow said toroidal pharmaceutical composition to remain substantially intact until contacting a target organ.

10. A toroidal aerosol delivery system, comprising:
    a gas reservoir chamber;
    an in-line aerosol generator adapted to deliver an aerosolized therapeutic agent;
    an orifice in fluid communication with said gas reservoir chamber and said in-line aerosol generator, said orifice adapted to emit a toroidal pharmaceutical composition; and
    an actuator in mechanical communication with said gas reservoir chamber adapted to transiently increase pressure within said aerosol chamber sufficient to emit a toroidal pharmaceutical composition comprising an aerosolized therapeutic agent within a toroidal vortex through the orifice, said toroidal vortex having a directional velocity and an internal rotational velocity, wherein the composition maintains its size and shape along an uncontained axis of propagation.

11. The toroidal aerosol delivery system of claim 10, wherein said actuator comprises a plurality of actuators, said plurality of actuators comprising a first actuator in mechanical communication with said gas reservoir chamber and a second actuator in mechanical or electrical communication with said in-line aerosol generator.

12. The toroidal aerosol delivery system of claim 10, wherein said actuator is adapted to provide a force resulting in a toroidal rotational velocity sufficiently high to allow said toroidal pharmaceutical composition to remain substantially intact until contacting a target organ.

13. The toroidal aerosol delivery system of claim 10, further comprising a first valve in fluid communication with said orifice, said first valve adapted for controlled passage of aerosolized therapeutic agent.

14. The toroidal aerosol delivery system of claim 10, further comprising a second valve in fluid communication with said gas reservoir chamber, said second valve adapted for controlled passage of air.

15. The toroidal aerosol delivery system of claim 10, wherein said actuator comprises a controller, wherein said controller is adapted to reproducibly provide a mechanical force.

16. A method for administering an aerosolized ophthalmically active pharmaceutical ingredient to a subject in need thereof, said method comprising administering an effective amount of a toroidal pharmaceutical composition to an eye of said subject, wherein said toroidal pharmaceutical composition comprises said aerosolized ophthalmically active pharmaceutical ingredient within a toroidal vortex until contacting said eye, said toroidal vortex having a directional velocity and an internal rotational velocity, wherein the composition maintains its size and shape along an uncontained axis of propagation.

17. The method of one claim 16, wherein said administering comprises
charging a toroidal aerosol delivery system, thereby providing a charged toroidal aerosol delivery system; and
actuating said toroidal aerosol delivery system, wherein said actuating provides a force resulting in a toroidal rotational velocity sufficiently high to allow said toroidal pharmaceutical composition to remain substantially intact until contacting said eye.

18. The method of claim 17, wherein said toroidal aerosol delivery system comprises:
an aerosol chamber;
an aerosol generator in fluid communication with said aerosol chamber, said aerosol generator adapted to charge said aerosol chamber with said aerosolized ophthalmically active pharmaceutical ingredient;
an orifice in fluid communication with said aerosol chamber, said orifice adapted to emit said toroidal pharmaceutical composition; and
an actuator in mechanical communication with said aerosol chamber adapted to transiently increase pressure within said aerosol chamber sufficient to emit said toroidal pharmaceutical composition through the orifice.

19. The method of claim 17, wherein said toroidal aerosol delivery system comprises:
a gas reservoir chamber;
an in-line aerosol generator adapted to deliver said aerosolized ophthalmically active pharmaceutical ingredient;
an orifice in fluid communication with said gas reservoir chamber and said in-line aerosol generator, said orifice adapted to emit said toroidal pharmaceutical composition; and
an actuator in mechanical communication with said gas reservoir chamber adapted to transiently increase pressure within said gas reservoir chamber sufficient to emit said toroidal pharmaceutical composition through the orifice.

\* \* \* \* \*